(12) United States Patent
Bermudes

(10) Patent No.: US 8,771,669 B1
(45) Date of Patent: *Jul. 8, 2014

(54) IMMUNIZATION AND/OR TREATMENT OF PARASITES AND INFECTIOUS AGENTS BY LIVE BACTERIA

(76) Inventor: David Gordon Bermudes, Woodland Hills, CA (US)

(*) Notice: Subject to any disclaimer, the term of this patent is extended or adjusted under 35 U.S.C. 154(b) by 326 days.

This patent is subject to a terminal disclaimer.

(21) Appl. No.: 13/024,189

(22) Filed: Feb. 9, 2011

Related U.S. Application Data

(60) Provisional application No. 61/302,834, filed on Feb. 9, 2010.

(51) Int. Cl.
*A61K 35/74* (2006.01)
*A61K 39/00* (2006.01)
*C12R 1/00* (2006.01)
*C12R 1/42* (2006.01)

(52) U.S. Cl.
USPC ............ 424/93.2; 424/93.4; 435/252.3

(58) Field of Classification Search
USPC ................. 424/93.4; 435/252.1, 252.3
See application file for complete search history.

(56) References Cited

U.S. PATENT DOCUMENTS

| | | | |
|---|---|---|---|
| 8,241,623 B1 * | 8/2012 | Bermudes | 424/93.4 |
| 2005/0158295 A1 * | 7/2005 | Swiercz et al. | 424/94.3 |

FOREIGN PATENT DOCUMENTS

WO WO 01/25397 * 4/2001

OTHER PUBLICATIONS

Shiga et al, Applied & Environ. Microbiol. 58(2):525-531, 1992.*
Taguchi et al, Biochim. Biophys. Acta 1049(3):278-285, 1990; abstract only.*
McClelland et al, GenBank AAL21164.1; 2001.*

* cited by examiner

*Primary Examiner* — Kevin Hill
(74) *Attorney, Agent, or Firm* — Steven M. Hoffberg; Ostrolenk Faber LLP

(57) ABSTRACT

Chimeric proteins are expressed, secreted or released by a bacterium to immunize against or treat a parasite, infectious disease or malignancy. The delivery vector may also be attenuated, non-pathogenic, low pathogenic, or a probiotic bacterium. The chimeric proteins include chimeras of, e.g., phage coat and/or colicin proteins, bacterial toxins and/or enzymes, autotransporter peptides, lytic peptides, multimerization domains, and/or membrane transducing (ferry) peptides. The active portion of the immunogenic chimeric proteins can include antigens against a wide range of parasites and infectious agents, cancers, Alzheimer's and Huntington's diseases, and have enhanced activity when secreted or released by the bacteria, and/or have direct anti-parasite or infectious agent activity. The activity of the secreted proteins is further increased by co-expression of a protease inhibitor that prevents degradation of the effector peptides. Addition of an antibody binding or antibody-degrading protein further prevents the premature elimination of the vector and enhances the immune response.

19 Claims, 3 Drawing Sheets

Figure 1:
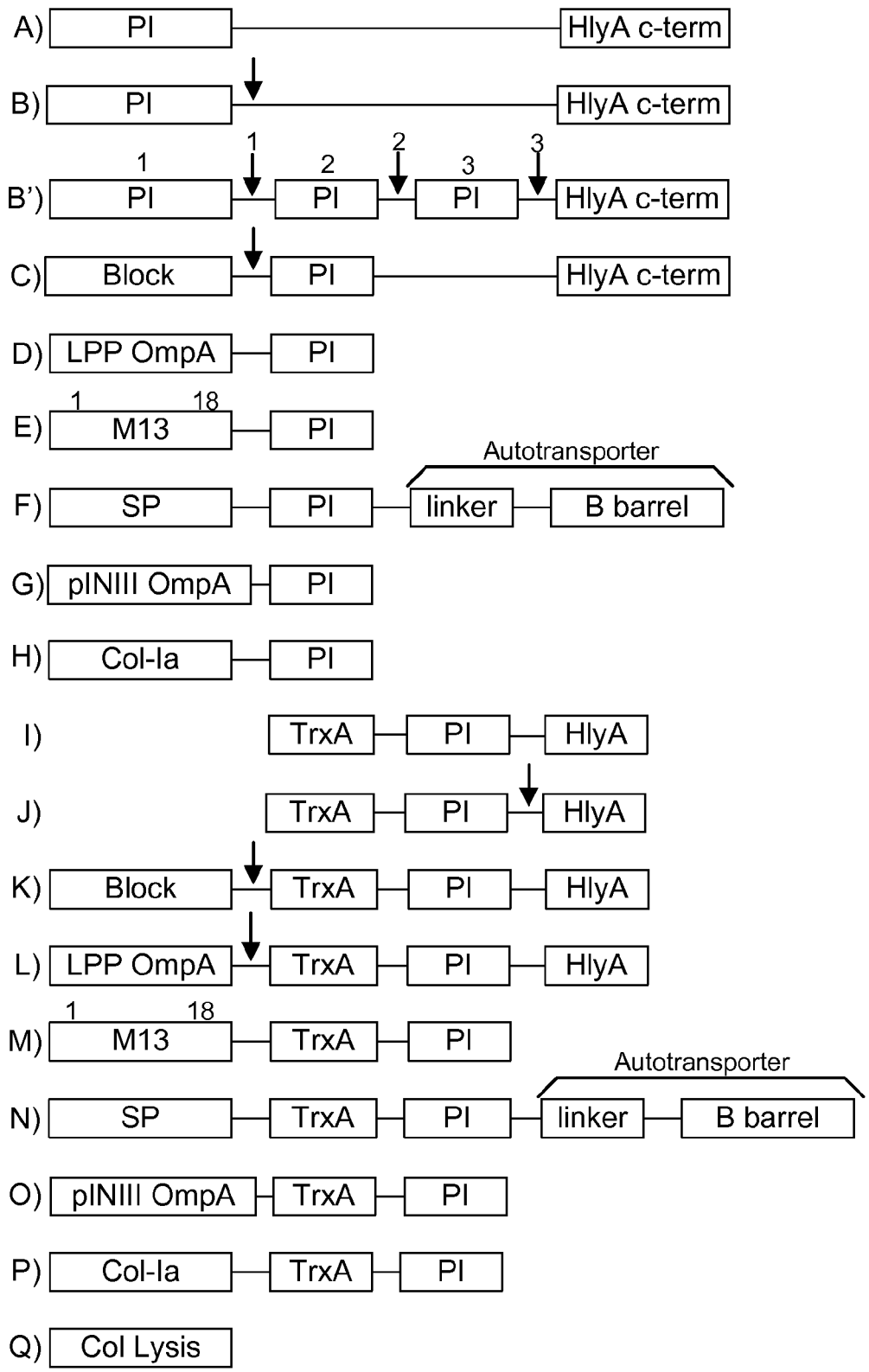

IMMUNIZATION AND/OR TREATMENT OF PARASITES AND INFECTIOUS AGENTS BY LIVE BACTERIA

1. FIELD OF THE INVENTION

This invention is related to the field of anti-infective therapeutics, therapeutic delivery systems, and methods for providing live bacterial vaccines against infectious diseases.

2. BACKGROUND OF THE INVENTION

Citation or identification of any reference herein, or any section of this application shall not be construed as an admission that such reference is available as prior art to the present application. The disclosures of each of the publications cited herein, are hereby incorporated by reference in their entirety in this application, and shall be treated as if the entirety thereof forms a part of this application.

Worldwide, infectious diseases cause greater than one third of all deaths, more than any other group of related causes. Vaccines offer one of the greatest means of preventing infectious diseases. Unfortunately, many diseases remain without effective vaccines, or have treatments for which developing countries cannot afford. New vaccines, vaccine carriers, adjuvants, delivery methods and novel therapeutics are needed in order to meet the worldwide challenge of infectious diseases.

The use of live attenuated bacteria as carriers for delivering heterologous antigens from other infectious diseases is considered a promising methodology, yet remains without any products approved for clinical use more than 20 years after the concept was first developed (see Kotton and Hohmann 2004, Infection and Immunity 72: 5535-5547 and Roland et al., 2005, Current opinion in Molecular Therapeutics 7: 62-72 for reviews). Among the considerations for achieving therapeutic efficacy by such live attenuated bacterial vaccines delivering heterologous antigens is the secretion of sufficient quantities of the immunogenic antigen which is then capable of leading to a productive immune response. Similar hurdles also exist for therapeutic vectors secreting one or more anti-infective proteins or immunomodulatory cytokines such as IL-10 (Steidler and Rottiers, 2006, "Annals of the New York Academy of Sciences 1072:176-186.; Neirynck and Steidler 2006, Biotechnology & Genetic Engineering Reviews 22: 253-66; Steidler 2005," Expert opinion on drug delivery 2:737-46).

Most infectious disease agents gain entrance to the host through a mucosal surface, and therefore the first line of defense is the mucosal immune system. In fact, protection against many microorganisms better correlates with local rather than systemic immune responses (Galan et al., 1986, Infection & Immunity 54:202-206; Galan and Timoney 1985, Infection & Immunity 47:623-628). Live, replicating agents are known to better stimulate mucosal immunity partly because they tend to persist longer (Ganguly and Waldman, Prog Allergy 27:1-68 (1980).

Avirulent strains of *Salmonella* endowed with the ability to express cloned genes from other pathogens have been used to stimulate a generalized mucosal immune response against the recombinant virulence antigens (Doggett and Curtiss 1992, Adv Exp Med Biol 327:165-173; Curtiss et al., 1988, in Virulence Mechanisms of Bacterial Pathogenesis, R. Roth, Ed., pp. 311-328; Curtiss et al., 1990, Res Microbiol 141:797-805). However, the use of replicating bacteria to stimulate mucosal immune responses has been hampered by secretion of antigens that effectively induce secretory immunity. For a review of secretion fusion systems, see Ni and Chen 2009 (Biotechnol. Lett 31: 1661-1670).

Use of secreted proteins in live bacterial vectors has been demonstrated by several authors. Holland et al. (U.S. Pat. No. 5,143,830, expressly incorporated in its entirety herein by reference) have illustrated the use of fusions with the C-terminal portion of the hemolysin A (hlyA) gene, a member of they type I secretion system. When co-expressed in the presence of the hemolysin protein secretion channel (hlyBD) and a functional TolC, heterologous fusions are readily secreted from the bacteria. The type I secretion system that has been utilized most widely, and although it is currently considered the best system available, is thought to have limitations for antigen delivery by attenuated bacteria (Hahn and Specht, 2003, FEMS Immunology and Medical Microbiology, 37: 87-98). Those limitations include the amount of protein secreted and the ability of the protein fused to it to interfere with secretion. Improvements of the type I secretion system have been demonstrated by Sugamata and Shiba (2005 Applied and Environmental Microbiology 71: 656-662) using a modified hlyB, and by Gupta and Lee (2008 Biotechnology and Bioengineering, 101: 967-974) by addition of rare codons to the hlyA gene. Fusion to the gene ClyA (Galen et al., 2004, Infection and Immunity, 72: 7096-7106 and Type III secretion proteins have also been used. Other heterologous protein secretion systems include the use of the autotransporter family (see Jose, 2006 Applied Microbiol. Biotechnol. 69: 607-614 and Rutherford and Mourez 2006 Microbial Cell Factories 5: 22). For example, Veiga et al. (2003 Journal of Bacteriology 185: 5585-5590 and Klauser et al., 1990 EMBO Journal 9: 1991-1999) demonstrated hybrid proteins containing the β-autotransporter domain of the immunoglogulin A (IgA) protease of *Neisseria gonorrhea*. Fusions to flagellar proteins have also been shown to be immunogenic. The antigen, a peptide, usually of 15 to 36 amino acids in length, is inserted into the central, hypervariable region of the FliC gene such as that from *Salmonella muenchen* (Verma et al. 1995 Vaccine 13: 235-24; Wu et al., 1989 Proc. Natl. Acad. Sci. USA 86: 4726-4730; Cuadro et al., 2004 Infect. Immun. 72: 2810-2816; Newton et al., 1995, Res. Microbiol. 146: 203-216). Antigenic peptides are selected by various methods, including epitope mapping (Joys and Schodel 1991. Infect. Immune. 59: 3330-3332; Hioe et al., 1990 J. Virol. 64: 6246-6251; Kaverin et al. 2002, J. Gen. Virol. 83: 2497-2505; Hulse et al. 2004, J. Virol. 78: 9954-9964; Kaverin et al. 2007, J. Virol. 81:12911-12917), T-cell epitope determination (Walden, 1996, Current Opinion in Immunology 8: 68-74) and computer programs such as Predict7 (Carmenes et al. 1989 Biochem. Biophys. Res. Comm 159: 687-693) Pepitope (Mayrose et al., 2007. Bioinformatics 23: 3244-3246). Multihybrid FliC insertions of up to 302 amino acids have also been prepared and shown to be antigenic (Tanskanen et al. 2000, Appl. Env. Microbiol. 66: 4152-4156). Trimerization of antigens has been achieved using the T4 fibritin foldon trimerization sequence (Wei et al. 2008 J. Virology 82: 6200-6208) and VASP tetramerization domains (Kühnel et al., 2004 PNAS 101: 17027-17032). As noted above, each of the foregoing and following references is expressly incorporated by reference in its entirety herein.

Other technologies employing bacteria have also been explored as methods to create vaccines. U.S. Pat. No. 6,177,083 by Lubitz, expressly incorporated herein by reference, describes the use of membrane disruptive proteins or bacteriophages to create non-living, non-replicative "bacterial ghosts"; bacterial fragments that contain the desired antigen. However, bacterial ghosts are generally less immunogenic than live bacteria, and multiple doses with larger quantities are required since they do not replicate. To date, none have entered clinical trials.

In addition to combating parasitic or infectious diseases using vaccines, anti-infectious agents are used to directly to treat infections. For example, Ivermenctin (22, 23-dihydroavermectin $B_{1a}$+22, 23-dihydroavermectin $B_{1b}$), marketed under the brand name Mectizan, is currently being used to help eliminate river blindness (onchocerciasis) in the Americas and stop transmission of lymphatic filariasis and onchocerciasis around the world. However, the number of effective anti-parasitic therapies is few, and many would-be anti-parasitic compounds are ultimately found to be unsuitable for use in humans and other mammals or birds because they are not effective at reaching the site of infection. Even though bacteria such as *Salmonella, Enterococcus* and *Escherichia* are known to be able to infect nematodes such as *Caenorhabdus elegans*, they have not been suggested as antiparasitic vectors capable of delivering anti-infective proteins nor has the desirability of such a system been recognized. New methods to deliver anti-parasitic drugs directly to the site of infection would greatly enhance their effectiveness.

Although bacteria have been used as vaccine for infectious diseases, it has not been recognized that they could be modified to serve as direct anti-infective agents with the ability to deliver anti-infective proteins. Furthermore, the usefulness of bacterial vaccine vectors has remained to be fulfilled, perhaps in part because the inability to prevent degradation of effector proteins following secretion. Copious secretion and sustained activity of antigens and/or anti-parasitic peptides through their stabilization by protease inhibitors expressed by attenuated bacteria that result in effective vaccines or therapeutic vectors has not previously been achieved.

3. SUMMARY OF THE INVENTION

One embodiment of the present invention comprises novel chimeric proteins, or combinations of proteins, that are expressed, secreted or released by bacteria and result in antiparasitic, anti-infectious agent or anti-malignancy immune responses by the host, or have direct inhibitory or cytotoxic anti-parasitic or anti-infectious agent activity, and the production, and use thereof. The bacterial delivery vector may be attenuated, non-pathogenic, low pathogenic, or a probiotic bacterium. The bacteria are introduced either systemically (e.g., parenteral, intravenous, intramuscular, intralymphatic, intradermal, subcutaneous) or to the mucosal system through oral, nasal, intravessically or suppository administration where they are able to undergo limited replication, express, secrete or release the immune-stimulating or anti-parasitic inhibitory proteins or a combination thereof, and thereby provide a therapeutic benefit to the host by reducing or eliminating the targeted parasite, infectious disease or malignancy.

The parasites or infectious agents to which the immune-stimulating antigens, anti-parasitic inhibitory or cytotoxic proteins relate can include viruses, bacteria, fungi, protozoans (protists) helminthes, nematodes, trematodes, cestodes and prions such as DNA Viruses, Poxyiridae, Parapoxviruses, Molluscum Contagiosum, Tanapox, Herpesviridae, Herpes Simplex Virus, Varicella-Zoster Virus, Cytomegalovirus, Epstein-Barr Virus (Infectious Mononucleosis), Human Herpesvirus Types 6 and 7, Kaposi's Sarcoma-Associated Herpesvirus (Human Herpesvirus Type 8), Herpes B Virus—Adenoviridae, Adenovirus—Papovaviridae, Papillomaviruses, JC, BK, and other Polyomaviruses; Progressive Multifocal Leukoencephalopathy—Hepadnaviridae, Hepatitis B Virus and Hepatitis Delta Virus—Parvoviridae, Human Parvoviruses—RNA Viruses, Reoviridae, Orthoreoviruses and Orbiviruses, Coltiviruses and Seadornaviruses (Colorado Tick Fever), Rotaviruses—Togaviridae, Alphaviruses, Rubella Virus (German Measles)—Flaviviruses, Flaviviruses (Yellow Fever, Dengue, Dengue Hemorrhagic Fever, Japanese Encephalitis, West Nile Encephalitis, St. Louis Encephalitis, Tick-Borne Encephalitis), Hepatitis C—Coronaviridae, Coronaviruses, Including SARS-Associated Coronavirus, Paramyxoviridae, Parainfluenza Viruses, Mumps Virus, Respiratory Syncytial Virus (RSV), Human Metapneumovirus, Measles Virus (Rubeola), Zoonotic Paramyxoviruses Hendra, Nipah, and Menangle Viruses, Rhabdoviridae, Vesicular Stomatitis Virus and Related Viruses, Rhabdoviruses—Filoviridae, Marburg and Ebola Virus Hemorrhagic Fevers—Orthomyxoviridae, Influenza Viruses including Avia Hemorrhagic Fevers—Arenaviridae, Lymphocytic Choriomeningitis Virus, Lassa Virus, and the South American Hemorrhagic Fevers—Retroviridae, Human T-Cell Lymphotropic Virus Types I and II, Human Immunodeficiency Viruses—Picornaviridae, Enteroviruses, Poliovirus, Coxsackieviruses, Echoviruses, Hepatitis A Virus—Caliciviridae and other Gastrointestinal Viruses, Rhinovirus, Noroviruses and other Caliciviruses, Astroviruses and Picobirnaviruses—unclassified viruses, Hepatitis E Virus, Prions and Prion Diseases of the Central Nervous System (Transmissible Neurodegenerative Diseases), *Chlamydia trachomatis* (Trachoma, Perinatal Infections, Lymphogranuloma Venereum, and other genital infections), *Chlamydophila (Chlamydia) psittaci* (Psittacosis), *Chlamydophila (Chlamydia) pneumoniae, Mycoplasma pneumoniae* and atypical Pneumonia, genital Mycoplasmas: *Mycoplasma genitalium, Mycoplasma hominis*, and *Ureaplasma* Species, Rickettsioses, Ehrlichioses and Anaplasmosis, *Rickettsia rickettsii* and other Spotted Fever Group Rickettsiae (Rocky Mountain Spotted Fever and other spotted fevers), *Rickettsia akari* (Rickettsialpox), *Coxiella burneti* Typhus), *Rickettsia typhi* (Murine Typhus), Orientia Tsutsugamushi, Chaffeensis and *Ehrlichia Phagocytophila*, Gram-Positive Cocci, *Staphylococcus aureus* (including Staphylococcal Toxic Shock), *Staphylococcus epidermidis* and other Coagulase-Negative Staphylococci, Classification of Streptococci, *Streptococcus pyogenes*, nonsuppurative post-streptococcal sequelae: Rheumatic Fever and Glomerulonephritis, *Streptococcus pneumoniae, Enterococcus* Species, *Streptococcus bovis*, and *Leuconostoc* species, *Streptococcus agalactiae* (Group B *Streptococcus*), Viridans Streptococci, Groups C and G Streptococci, and *Gemella morbillorum, Streptococcus anginosus* Group—Gram-Positive Bacilli, *Corynebacterium diphtheriae*, Corynebacteria other than Diphtheria and *Rhodococcus, Listeria monocytogenes, Bacillus anthracis* (Anthrax), *Bacillus* species and other than *Bacillus anthracis, Erysipelothrix rhusiopathiae*—Gram-Negative Cocci, *Neisseria meningitides, Neisseria gonorrhoeae, Moraxella catarrhalis* and other Gram-Negative Cocci—Gram-Negative Bacilli, *Vibrio cholerae*, other pathogenic Vibrios, *Campylobacter jejuni* and related species, *Helicobacter pylori* and other gastric *Helicobacter* species, Enterobacteriaceae, *Pseudomonas* species, including *Ps. aeruginosa, Stenotrophomonas maltophilia* and *Burkholderia cepacia* complex, *Burkholderia pseudomalle, Salmonella typhi, Shigella* species (bacillary dysentery), *Haemophilus* species (including *H. influenzae* and chancroid), *Brucella* species, *Francisella tularensis* (Tularemia), *Pasteurella* species, *Yersinia* species, including plague, *Bordetella Pertussis*, Rat-Bite Fever *Streptobacillus moniliformis* and *Spirillum minus, Legionella*, other *Legionella* species, *Capnocytophaga, Bartonella*, including Cat-Scratch Disease, *Calymmatobacterium granulomatis* (Donovanosis, Granuloma Inguinale), other Gram-Negative and Gram-variable bacilli, Spirochetes, *Treponema pallidum* (Syphilis), Endemic Treponematoses, *Leptospira* Species (leptospirosis), *Borrelia* Species (Relapsing Fever), *Borrelia burgdorferi* (Lyme Disease, Lyme Borreliosis), anaerobic bacteria, *Clostridium tetani* (Tetanus), *Clostridium botulinum* (Botulism), gas gangrene and other *Clostridium*-associated diseases, *Bacteroides, Prevotella, Porphyromonas,* and *Fusobacterium* species, anaerobic cocci; anaerobic Gram-Positive non-sporulating bacilli, mycobacterial diseases, *Mycobacterium tuberculosis, Mycobacterium leprae, Mycobacterium Avium*-intracellulare, infections due to Mycobacteria other than *M. tuberculosis* and *M. Avium* Complex, *Nocardia* species, agents of Actinomycosis, mycoses, Chromomycosis agents of Mycetoma, *Cryptococcus neoformans, Histoplasma capsulatum, Blastomyces dermatitidis, Coccidioides* species, Dermatophytosis and other superficial mycoses, *Paracoccidioides brasiliensis, Prototheca, Pneumocystis,* Microsporidiosis, protozoal diseases, *Entamoeba* species including amoebiasis, free-living amebas, *Plasmodium* species (Malaria), *Leishmania* Species: visceral, cutaneous, and mucocutaneous Leishmaniasis, *Trypanosoma* species, agents of African Trypanosomiasis (Sleeping Sickness), *Toxoplasma gondii, Giardia lamblia, Trichomonas vaginalis, Babesia* species, *Cryptosporidium* species, *Isospora belli, Sarcocystis* species, *Blastocystis hominis, Cyclospora*, illness associated with harmful algal blooms, helminth infections, intestinal nematodes (roundworms), tissue nematodes including Trichinosis, Dracunculiasis, and the Filariases, Trematodes (Schistosomes and Other Flukes), Cestodes (Tapeworms), Visceral Larva Migrans and other unusual helminth infections, ectoparasitic diseases, lice (Pediculosis), Scabies, Myiasis and Tungiasis, and mites (including Chigger Syndrome).

The immunostimulatory effects may also be directed toward other diseases such as Alzheimer's and Huntington's disease or cancer. The cancers may include solid tumors, leukemias and lymphomas, including acute lymphoblastic leukemia, acute myeloid leukemia, adrenocortical carcinoma adrenocortical carcinoma, AIDS-related cancers, AIDS-related lymphoma, anal cancer, appendix cancer, astrocytomas, childhood, teratoid/rhabdoid tumor, childhood, central nervous system tumors, basal cell carcinoma, bile duct cancer, extrahepatic bladder cancer, bladder cancer, bone cancer, osteosarcoma and malignant fibrous histiocytoma, brain stem glioma, brain tumor, brain stem glioma, central nervous system atypical teratoid/rhabdoid tumor, central nervous system embryonal tumors, brain tumor, astrocytomas, craniopharyngioma, ependymoblastoma, ependymoma, medulloblastoma, medulloepithelioma, pineal parenchymal tumors, supratentorial primitive neuroectodermal tumors and pineoblastoma, spinal cord tumors, breast cancer (female) breast cancer (male), bronchial tumors, burkitt lymphoma, carcinoid tumor, gastrointestinal, nervous system atypical teratoid/rhabdoid tumor, central nervous system embryonal tumors, central nervous system lymphoma, primary cervical cancer, cervical cancer, chordoma, chronic lymphocytic leukemia, chronic myelogenous leukemia, chronic myeloproliferative disorders, colon cancer, colorectal cancer, craniopharyngioma, cutaneous T-cell lymphoma, embryonal tumors, endometrial cancer, ependymoblastoma, ependymoma, esophageal cancer, ewing sarcoma family of tumors, extracranial germ cell tumor, extrahepatic bile duct cancer, eye cancer, intraocular melanoma, eye cancer, retinoblastoma gallbladder cancer, gastric (stomach) cancer, gastrointestinal carcinoid tumor, gastrointestinal stromal tumor (gist), gastrointestinal stromal cell tumor, germ cell tumor, extracranial germ cell tumor, extragonadal germ cell tumor, ovarian gestational trophoblastic tumor, glioma, hairy cell leukemia, head and neck cancer, hepatocellular (liver) cancer, primary hepatocellular (liver) cancer, histiocytosis, langerhans cell, hodgkin lymphoma, hypopharyngeal cancer, intraocular melanoma, islet cell tumors (endocrine pancreas), kaposi sarcoma, kidney (renal cell) cancer, kidney cancer, langerhans cell histiocytosis, laryngeal cancer, leukemia, acute lymphoblastic leukemia, acute myeloid leukemia, chronic lymphocytic leukemia, chronic myelogenous leukemia, hairy cell leukemia, lip and oral cavity cancer, liver cancer, adult (primary) liver cancer, (primary) lung cancer, non-small cell lung cancer, small cell lymphoma, aids-related lymphoma, burkitt lymphoma, cutaneous T-cell lymphoma, hodgkin lymphoma, non-hodgkin lymphoma, primary central nervous system lymphoma, macroglobulinemia, waldenström malignant fibrous histiocytoma of bone and osteosarcoma, medulloblastoma, melanoma, intraocular (eye) melanoma, merkel cell carcinoma, mesothelioma, metastatic squamous neck cancer with occult primary, mouth cancer, multiple endocrine neoplasia syndrome, childhood multiple myeloma/plasma cell neoplasm, mycosis fungoides, myelodysplastic syndromes, myelodysplastic/myeloproliferative diseases, myelogenous leukemia, chronic myeloid leukemia, adult acute myeloid leukemia, childhood acute myeloma, multiple myeloproliferative disorders, nasal cavity and paranasal sinus cancer, nasopharyngeal cancer, nasopharyngeal cancer, neuroblastoma, non-hodgkin lymphoma, non-small cell lung cancer, oral cancer, oral cavity cancer, lip and oropharyngeal cancer, osteosarcoma and malignant fibrous histiocytoma of bone, ovarian cancer, ovarian epithelial cancer, ovarian germ cell tumor, ovarian low malignant potential tumor, pancreatic cancer, islet cell tumors, papillomatosis, paranasal sinus and nasal cavity cancer, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, renal pelvis and ureter, transitional cell cancer, respiratory tract carcinoma involving the nut gene on chromosome 15, retinoblastoma, rhabdomyosarcoma, salivary gland cancer, sarcoma, ewing sarcoma family of tumors, kaposi sarcoma, soft tissue sarcoma, uterine sarcoma, Sézary syndrome, skin cancer (nonmelanoma), melanoma, skin carcinoma, merkel cell, small cell lung cancer, small intestine cancer, soft tissue sarcoma, squamous cell carcinoma, see skin cancer (nonmelanoma), squamous neck cancer with occult primary, metastatic stomach (gastric) cancer, stomach (gastric) cancer, supratentorial primitive neuroectodermal tumors, T-cell lymphoma, cutaneous T-cell lymphoma, mycosis fungoides and Sézary syndrome, testicular cancer, throat cancer, thymoma and thymic carcinoma, thyroid cancer, transitional cell cancer of the renal pelvis and ureter, trophoblastic tumor, (gestational), unknown primary site, carcinoma of, unknown primary site carcinoma, ureter and renal pelvis, transitional cell cancer, urethral cancer, uterine cancer, endometrial uterine sarcoma, vaginal cancer, vulvar cancer, Waldenström macroglobulinemia, and wilms tumor.

The process of the immune-stimulating presence of bacteria and possible pathways for the induction of IgA responses in the gut is described by Fagarasan (2008, Current Opinion in Immunology 20: 170-177; Suzuki and Fagarasan, 2008, Trends in Immunology 29: 523-531). Within gut follicular structures (i.e. Peyer's patches) antigens from bacteria lead to the stimulation of antibody-producing B-cells. Alternatively, B-cells are activated at the lamina propria by antigens presented by the dendritic cells or by polyclonal stimuli. One embodiment of the present invention provides bacteria that supply specific antigens together with protease inhibitors that prevent their destruction by digestive and/or proteases, yet allows antigen processing by dendridic cell cathepsins that would lead to cellular responses (described below). Alternatively, the bacteria may specifically inhibit cathepsins limiting cellular responses, and enhance mucosal immunity via the production of antibodies. For example, human studies have shown that antibody titres against hemagglutinin of human influenza virus are correlated with protection (a serum sample hemagglutination-inhibition titre of about 30-40 gives around 50% protection from infection by a homologous virus) (Potter & Oxford (1979) Br Med Bull 35: 69-75). Antibody responses are typically measured by enzyme linked immunosorbent assay (ELISA), immunoblotting, hemagglutination inhibition, by microneutralisation, by single radial immunodiffusion (SRID), and/or by single radial hemolysis (SRH). These assay techniques are well known in the art.

Cellular responses to vaccination may also occur which participate in anti-parasitic immunity. Cells of the immune system are commonly purified from blood, spleen or lymph nodes. Separate cell populations (lymphocytes, granulocytes and monocyte/macrophages and erythrocytes) are usually prepared by density gradient centrifugation through Ficoll-Hypaque or Percoll solutions. Separation is based on the buoyant density of each cell subpopulation at the given osmolality of the solution. Monocytes and neutrophils are also purified by selective adherence. If known subpopulations are to be isolated, for example CD4+ or CD8+ T cells, fluorescence activated cell sorting (FACS) will be employed or magnetic beads coated with specific anti-CD4 or anti-CD8 monoclonal antibody are used. The beads are mixed with peripheral blood leukocytes and only CD4+ or CD8+ cells will bind to the beads, which are then separated out from the non-specific cells with a magnet. Another method depends on killing the undesired populations with specific antibodies and complement. In some cases, a noncytotoxic antibody or other inhibitor can block the activity of a cell subtype. Characterization of cell types and subpopulations can be performed using markers such as specific enzymes, cell surface proteins detected by antibody binding, cell size or morphological identification. Purified or unseparated lymphocytes can be activated for proliferation and DNA synthesis is measured by $^3$H-thymidine incorporation. Other measures of activation such as cytokine production, expression of activation antigens, or increase in cell size are utilized. Activation is accomplished by incubating cells with nonspecific activators such as Concanavalin A, phytohemagglutinin (PHA), phorbol myristic acetate (PMA), an ionophore, an antibody to T cell receptors, or stimulation with specific antigen to which the cells are sensitized. Cellular responses may also be elicited through Toll-like Receptors (TLRs), including but not limited to TLRs 1-9 (Krieg, 2008 Oncogene 27: 161-167; O'Neill, Oncogene 27: 158-160; Spaner et al., 2008, Oncogene 27: 208-217. Targeting peptides may be used to modify the antigens such that they are targeted to immune processing cells such as dendritic cells.

A key activity of cellular immunity reactions to pathogens such as viruses is the development of T lymphocytes that specifically kill target cells, e.g., cytotoxic lymphocytes (CTLs). These activated cells develop during in vivo exposure or by in vitro sensitization. The CTL assay consists of increasing number of sensitized lymphocytes cultured with a fixed number of target cells that have been prelabeled with $^{51}$Cr. To prelabel the target cells, the cells are incubated with the radio-label. The $^{51}$Cr is taken up and reversibly binds to cytosolic proteins. When these target cells are incubated with sensitized lymphocytes, the target cells are killed and the $^{51}$Cr is released.

Natural killer (NK) cells are an essential defense in the early stage of the immune response to pathogens. NK cells are active in naïve individuals and their numbers can be enhanced in certain circumstances. The NK assay typically uses a $^{51}$Cr-labeled target and is similar to the CTL assay described above.

Specifically activated lymphocytes synthesize and secrete a number of distinctive cytokines. These are quantitated by various ELISA methods. Alternatively, induced cytokines are detected by fluorescence activated flow cytometry (FACS) using fluorescent antibodies that enter permeabilized cells. Activated cells also express new cell surface antigens where the number of cells is quantitated by immunofluorescent microscopy, flow cytometry, or ELISA. Unique cell surface receptors that distinguish cell populations are detected by similar immunochemical methods or by the binding of their specific labeled ligand.

Chimeric scaffolds useful in various embodiments of the present invention that can be modified uniquely to suit the delivery by a bacterium and may be engineered to have either antigenic or antiparasitic activity. Proteins from which the chimeras can be constructed include colicins, filamentous phage proteins, and protein toxins including autotransporter proteins. The colicins include but are not limited to ColE1, ColE1a, ColE1b ColE2, ColE3, ColE4, ColE5, ColE6, ColE7, ColE8, ColE9, Colicins A, Colicin K, Colicin L, Colicin M, cloacin DF13, pesticin A1122, staphylococcin 1580, butyricin 7423, pyocin R1 or AP41, megacin A-216, vibriocin and col-Ia. The filamentous phage proteins include but are not limited to M13 pIII, pVII, and pVIII. The protein toxins include but are not limited to, heat stable toxins (ST) from *Vibrio* and *Escherichia* or other enterobacteriaceae, autotransporter toxins including but not limited to IgA protease, picU espC, and sat, cytolethal distending toxin (cldt), typhoid toxin (pltAB), cldt:plt hybrids, cytotoxic nectrotic factor (cnf), dermonecrotic factor (dnf), shiga toxin and shiga-like toxins.

The chimeras may be further modified by addition of one or more trimerization domains, such as the T4 foldon (Meier et al., 2004, Journal of Molecular Biology, 344: 1051-1069; Bhardwaj et al., Protein Sci. 2008 17: 1475-1485) or tetramerization domains such as VASP (Kühnel et al., 2004 PNAS 101: 17027-17032). Chimeric toxins may be further modified by the addition of known cell penetrating (ferry) peptide which further improves their entry into target cells and may result in cell-mediated immunity in addition to antibody-mediated immunity. Cell penetrating peptides include those derived from the HIV TAT protein, the antennapedia homeodomain (penetraxin), Kaposi fibroblast growth factor (FGF) membrane-translocating sequence (MTS), herpes simplex virus VP22, hexahistidine, hexylysine, or hexaarginine.

The chimeric proteins may have one or more additional features or protein domains known to those skilled in the art which are designed to be active or catalytic domains that result in the death of the cell, allow or facilitate them being secreted or released by autolytic peptides such as colicin or bacteriaphage release peptides, have targeting peptides that direct them to the target cells, and protease cleavage sites for activation (e.g., release from parent peptide), and thoredoxin or glutation S-transferase (GST) fusions that improve solubility.

Small lytic peptides (less than 50 amino acids) are used to construct chimeric proteins for more than one purpose. The chimeric proteins containing lytic peptides may be directly cytotoxic for the particular parasite. Furthermore, the lytic peptides are useful in chimeric proteins for affecting release from the endosome. Useful small lytic peptides useful may be, for example, derived from *Staphylococcus aureus, S. epidermidis* and related species, including the phenol-soluble modulin (PSM) peptides and delta-lysin (Wang et al., 2007 Nature Medicine 13: 1510-1514). Larger lytic peptides that may be used includes the actinoporins from sea anemones or other coelenterates, such as SrcI, FraC equinatoxin-II and sticholysin-II (Anderluh and Macek 2002, Toxicon 40: 111-124). The selection of the lytic peptide depends upon the primary purpose of the construct, which may be used in combination with other constructs providing other anticancer features. Construct designed to be directly cytotoxic to cells employ the more cytoxic peptides, particularly PSM-alpha-3 or an actinoporin. Constructs which are designed to use the lytic peptide to affect escape from the endosome use the peptides with the lower level of cytotoxicity, such as PSM-alpha-1, PSM-alpha-2 or delta-lysin.

Other proteins with anti-infective activity include bacterial toxins with anti-insect and/or anti-parasite activity, including *Bacillus* BT toxins and the insecticidal cytotoxins form *Photorhabdus* and *Xenorhabdus* species, anthelmintic cyclic heptapeptide segetalin D (Dahiya 2007, Acta Pol. Pharm. 64: 509-516), cyclodepsipeptids (Dutton et al., J. Med. Chem. 46: 2057-2073) and toxins containing tyrosine and aspartic acid repeats (YD repeats).

Expression of antibody deactivating proteins are also encompassed by embodiments of the present invention. The antibody deactivating proteins serve to prevent the elimination of the bacterial vector, which, while generating an immune response to the heterologous infectious disease or parasite protein, also results in generating an immune response that would eliminate the bacterial vector. The antibody deactivating protein delays the elimination of the vaccine vector, resulting in a greater immune response. Antibody deactivating proteins include the IgA protease from *Neisseria* (when it is not being used as a fusion protein for secretion or surface display), IdeS, and EndoS proteases from *Staphalococcus*, the *Staphalococcus* antibody-binding protein A, and *Shistosoma* IgE proteases. The expression of the antibody deactivating proteins may be under transcriptional control by bacterial promoters that are inducible or constitutive.

The present invention provides, according to one embodiment, live attenuated therapeutic bacterial vaccine strains that express and secrete one or more therapeutic molecules that are chimeric proteins where the antigenic portion of the chimera is derived from an infectious agent and results in an immune response that reduces or eliminates the parasite, infectious agent, cancer or other malignancy including Alzheimer's or Huntington's diseases.

In another embodiment, the chimeric antigens are protease sensitive to proteases present at the site where the vaccine antigen is secreted, such as trypsin sensitivity for an antigen secreted in the gut, and the antigen is co-expressed with a secreted trypsin protease inhibitor, and encompasses co-expression of multiple proteases inhibitors when multiple proteases are present. In another embodiment, the secreted protease inhibitor, or multiple protease inhibitors, are novel chimeric secreted proteins.

In another embodiment, the invention provides live attenuated therapeutic bacterial strains that express and secrete one or more therapeutic molecules that are chimeric proteins where the therapeutic portion has direct cytolytic (lytic) anti-infective activity against one or more parasites. In another embodiment, the cytolytic protein is an in-frame fusion with a targeting peptide that directs it to the parasite. In another embodiment, the bacteria are engineered to inhibit local proteases that could deactivate the lytic molecules. In particular, one aspect of the invention relates to live attenuated bacterial strains that may include *Salmonella* vectoring chimeric lytic proteins with direct anti-infective activity to an individual to elicit a therapeutic response against the particular infective agent. In another embodiment, the bacteria may also contain heterologous proteins with anti-infective activity, that are not secreted.

In another embodiment, the invention provides live attenuated therapeutic bacterial strains that express and/or secrete one or more therapeutic molecules that are chimeric proteins where the therapeutic portion has cytotoxic or inhibitory anti-infective activity against one or more parasites. In another embodiment, the cytotoxic or inhibitory protein is an in-frame fusion with a targeting peptide that directs it to the parasite. In another embodiment, the bacteria are engineered to inhibit local proteases that could deactivate the therapeutic molecules. In particular, one aspect of the invention relates to live attenuated bacterial strains that may include *Salmonella* vectoring therapeutic proteins with direct anti-infective activity to an individual to elicit a therapeutic response against the particular infective agent. In another embodiment, the bacteria may also contain heterologous proteins with anti-infective activity that are not secreted Proteins with antiparasite activity include bacterial toxins with anti-insect and/or anti-parasite activity, including those from *Bacillus thuringiensis* (e.g., BT toxin) which have potential for treating parasites and infectious diseases (see Li et al., 2008, Biological Control, 47: 97-102; Li, et al., 2007, Plant Biotechnology Journal 5:455-464; Cappello, M. (2006) Proc. Natl. Acad. Sci. 103(41):15154-15159; Wei J. Z., 2003 Proc. Natl. Acad. Sci. 100:2760-2765, and U.S. Pat. No. 5,281,530, Genes encoding nematode-active toxins cloned from *Bacillus thuringiensis* isolate PS17). Secreted insecticidal toxins and phenol oxidase inhibitors including but not limited to stilbenes from *Photorhabdus* and *Xenorhabdus* species are also encompassed by aspects of the invention. Lectins with antiparasite activity such those proteins purified from the corms of *Pinellia ternata* and *Lycoris radiata*. Both *P. ternata* agglutinin (PTA) protein and *L. radiata* agglutinin (LRA) as are also encompassed (Gaofu et al., 2008, Journal of Invertebrate Pathology 98: 40-45).

These bacterial strains are attenuated or non-pathogenic, safe for administration to reptiles, birds and mammals, including humans, and result in protective or curative immunity, and/or direct inhibitory or cytotoxic activity against an infectious agent such when administered alone or in combination.

The bacteria according to a preferred embodiment of the present invention have little or no ability to undergo bacterial conjugation, limiting incoming and outgoing exchange of genetic material, whereas the prior art fails to limit exchange of genetic material. In addition, certain of the therapeutic molecules have co-transmission requirements that are distal to the therapeutic molecule location further limiting known forms of genetic exchange.

Aspects of the present invention also provide novel chimeric bacterial toxins particularly suited for expression by gram-negative bacteria. The toxins may have added targeting ligands that render them selectively cytotoxic for specific infectious agents.

Accordingly, administration to an individual, of a live *Salmonella* bacterial vector, in accordance with an aspect of the present invention, that is genetically engineered to express one or more chimeric, antigenic proteins as described herein which may be co-expressed with one or more inhibitory or cytotoxic proteins has the ability to stimulate an anti-infective immune response and/or inhibit or kill infectious agents, resulting in a therapeutic benefit.

A preferred composition will contain, for example, a sufficient amount of live bacteria expressing the protease inhibitors, chimeric antigens and/or directly therapeutic protein(s) to produce a therapeutic response in the patient. Accordingly, the attenuated *Salmonella* strains described herein are both safe and useful as live bacterial vectors that can be orally or systemically administered to an individual to provide therapeutic benefit against infectious diseases.

Although not wishing to be bound by any particular mechanism, an effective immune response in humans by administration of genetically engineered, attenuated strains of *Salmonella* strains as described herein may be due to the ability of such mutant strains to persist in the mucosal tissues, including the gut lymphoidal tissues and or Peyer's patches, and continuously produce antigens that are presented to the mucosa without being degraded due to the co-expression of one or more protease inhibitors. Bacterial strains useful in accordance with a preferred aspect of the invention may carry the ability to produce a therapeutic molecule from an exogenous plasmid, the endogenous virulence plasmid, or chromosomally integrated cassette that encodes and directs expression of one or more therapeutic molecules together with one or more protease inhibitors, as described herein. The protease inhibitors serve to prevent the destruction of the therapeutic molecule while within the mucosa, blood, tissue or within the infectious agent itself and/or the site of infection. The protease inhibitor may also directly inhibit the infectious agent. Thus the protease inhibitor system both increases activity of antigens and direct anti-infective agents, but may also directly provide anti-infective activity.

The serovars of *S. enterica* that may be used as the attenuated bacterium of the live compositions described in accordance with various embodiments herein include, without limitation, *Salmonella enterica* serovar *Typhimurium* ("*S. typhimurium*"), *Salmonella montevideo*, *Salmonella enterica* serovar *Typhi* ("*S. typhi*"), *Salmonella enterica* serovar *Paratyphi* B ("*S. paratyphi* 13"), *Salmonella enterica* serovar *Paratyphi* C ("*S. paratyphi* C"), *Salmonella enterica* serovar *Hadar* ("*S. hadar*"), *Salmonella enterica* serovar *Enteriditis* ("*S. enteriditis*"), *Salmonella enterica* serovar *Kentucky* ("*S. kentucky*"), *Salmonella enterica* serovar *Infantis* ("*S. infantis*"), *Salmonella enterica* serovar *Pullorurn* ("*S. pullorum*"), *Salmonella enterica* serovar *Gallinarum* ("*S. gallinarum*"), *Salmonella enterica* serovar *Muenchen* ("*S. muenchen*"), *Salmonella enterica* serovar *Anaturn* ("*S. anatum*"), *Salmonella enterica* serovar *Dublin* ("*S. dublin*"), *Salmonella enterica* serovar *Derby* ("*S. derby*"), *Salmonella enterica* serovar *Choleraesuis* var. *kunzendorf* ("*S. cholerae kunzendorf*"), and *Salmonella enterica* serovar *minnesota* (*S. minnesota*).

Novel strains are also encompassed that are, for example, attenuated in virulence by mutations in a variety of metabolic and structural genes. The invention therefore may provide, according to some embodiments, a live composition for treating cancer comprising a live attenuated bacterium that is a serovar of *Salmonella enterica* comprising an attenuating mutation in a genetic locus of the chromosome of said bacterium that attenuates virulence of said bacterium and wherein said attenuating mutation is a combination of other known attenuating mutations. Other attenuating mutation useful in the *Salmonella* bacterial strains described herein may be in a genetic locus selected from the group consisting of phoP, phoQ, edt, cya, crp, poxA, rpoS, htrA, nuoG, pmi, pabA, pts, damA, pur, purA, purB, purI, purF, zwf, aroA, aroB, aroC, aroD, serC, gua, cadA, rfc, rjb, rfa, ompR, msbB, pfkAB, crr, glk, ptsG, ptsHI, manXYZ and combinations thereof. The strain may also contain a mutation known as "Suwwan", which is an approximately 100 kB deletion between two IS200 elements. The strain may also carry a defective thioredoxin gene (trxA−), a defective glutathione oxidoreductase (gor−) and optionally, overexpress a protein disulfide bond isomerase (DsbA). In a preferred embodiment, the strains are msbB mutants (msbB−). In a more preferred embodiment, the strains are msbB− and Suwwan. In a more preferred embodiment the strains are msbB−, Suwwan and zwf−. Zwf has recently been shown to provide resistance to $CO_2$, acidic pH and osmolarity (Karsten et al., 2009, BMC Microbiology August 18; 9:170). In a more preferred embodiment, the strains are msbB−, Suwwan, zwf− and trxA−. In a most preferred embodiment, the strains are msbB−, Suwwan, zwf−, trxA− and gor−.

By way of example, live bacteria in accordance with aspects of the invention include known strains of *S. enterica* serovar *Typhimurium* (*S. typhimurium*) and *S. enterica* serovar *Typhi* (*S. typhi*) which are further modified as provided by the invention to form suitable vaccines for the prevention and treatment of avian influenza. Such Strains include Ty21a, CMV906, CMV908, CMV906-htr, CMV908-htr, Ty800, aroA-/serC-, holavax, M01ZH09, VNP20009. These strains contain defined mutations within specific serotypes of bacteria. Embodiments of the invention may also include the use of these same mutational combinations contained within alternate serotypes or strains in order to avoid immune reactions which may occur in subsequent administrations. In a preferred embodiment, *S. Typhimurium*, *S. montevideo*, and *S. typhi* which have non-overlapping O-antigen presentation (e.g., *S. typhimurium* is O-1, 4, 5, 12 and *S. typhi* is Vi, *S. montevideo* is O-6, 7) may be used. Thus, for example, *S. typhimurium* is a suitable serotype for a first injection and another serotype such as *S. typhi* or *S. montevideo* are used for a second injection and third injections Likewise, the flagellar antigens are also selected for non-overlapping antigenicity between different injections. The flagellar antigen may be H1 or H2 or no flagellar antigen, which, when combined with the three different O-antigen serotypes, provides three completely different antigenic profiles.

Other bacterial strains are also encompassed, including non-pathogenic bacteria of the gut such as *E. coli* strains, Bacteriodies, *Bifidobacterium* and *Bacillus*, attenuated pathogenic strains of *E. coli* including enteropathogenic and uropathogenic isolates, *Enterococcus* sp. and *Serratia* sp. as well as attenuated *Neisseria* sp., *Shigella* sp., *Staphalococcus* sp., *Yersinia* sp., *Streptococcus* sp. and *Listeria* sp. Bacteria of low pathogenic potential to humans such as insect pathogenic *Xenorhabdus* sp., *Photorhabdus* sp. and human wound *Photorhabdus* (*Xenorhabdus*) are also encompassed. Probiotic strains of bacteria are also encompassed, including *Lactobacillus* sp., *Lactococcus* sp., *Leuconostoc* sp., *Pediococcus* sp., *Streptococcus* sp. *Lactococcus* sp., *Bacillus* sp., *Bifidobacterium* sp., *Bacteroides* sp., and *Escherichia coli* such as the 1917 Nissel strain. It is known to those skilled in the art that minor variations in molecular biology techniques such as use of gram-positive origins of replication, gram-positive signal sequences gram-positive promoters (e.g., *Lactococcus* expression, Mohamadzadeh et al., PNAS Mar. 17, 2009 vol. 106 no. 11 4331-4336) are required and substituted as needed.

The invention also provides, according to one embodiment, a bacterially codon optimized expression sequence within a bacterial plasmid expression vector or chromosomal or endogenous virulence plasmid localization expression vector for any intergenic region, defective phage components, or deleted bacterial chromosomal genes within the strain. Administration of the strain to the patient is therapeutic for one or more infectious diseases, parasites or malignancies including Alzheimer's and Huntington's diseases.

The present invention provides, for example, and without limitation, live bacterial compositions that are genetically engineered to express one or more protease inhibitors combined with effector molecules capable of delivering chimeric protein therapeutics for the prevention or treatment of infectious diseases.

According to various embodiments, the invention provides pharmaceutical compositions comprising pharmaceutically acceptable carriers and one or more bacterial mutants. The invention also provides pharmaceutical compositions comprising pharmaceutically acceptable carriers and one or more bacterial mutants comprising nucleotide sequences encoding one or more therapeutic molecules. The pharmaceutical compositions of various embodiments of the invention may be used in accordance with the methods of the invention for the prophylaxis or treatment of an infectious disease. Preferably, the bacterial mutants are attenuated by introducing one or more mutations in one or more genes in the lipopolysaccharide (LPS) biosynthetic pathway (for gram-negative bacteria), and optionally one or more mutations to auxotrophy for one or more nutrients or metabolites.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule is an antigen.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule is a molecule with direct anti-parasitic lytic capability.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule has direct anti-parasitic cytotoxic or inhibitory ability.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules co-expressed with a protease inhibitor.

In a specific embodiment, a pharmaceutical composition comprises a pharmaceutically acceptable carrier and one or more attenuated bacterial mutants, wherein the bacterial mutants are a *Salmonella* sp. In another specific embodiment, a pharmaceutical composition comprises a pharmaceutically acceptable carrier and one or more attenuated stress-resistant gram-negative bacterial mutants, wherein the attenuated stress-resistant gram-negative bacterial mutants are a *Salmonella* sp., and the attenuated stress-resistant gram-negative bacterial mutants comprise one or more nucleic acid molecules encoding one or more therapeutic molecules, antigens, lytic peptides or anti-parasitic peptides.

The present invention encompasses treatment protocols that provide a better therapeutic effect than current existing vaccines or antiparasitic therapies. In particular, some embodiments of the present invention provide methods for prophylaxis or treatment of parasitic diseases in a subject comprising administering to said subject and one or more stress-resistant gram-negative bacterial mutants, preferably attenuated stress-resistant gram-negative bacterial mutants. Some embodiments of the present invention also provide methods for the prophylaxis or treatment of virally induced disease in a subject comprising administering to said subject one or more stress-resistant gram-negative bacterial mutants, preferably attenuated stress-resistant gram-negative bacterial mutants, wherein said stress-resistant gram-negative bacterial mutants comprise one or more nucleic acid molecules encoding one or more therapeutic molecules.

The methods of the some embodiments of the present invention permit lower dosages and/or less frequent dosing of stress-resistant gram-negative bacterial mutants (preferably attenuated stress-resistant gram-negative bacterial mutants) to be administered to a subject for prophylaxis or treatment of virally induced disease to achieve a therapeutically effective amount of one or more therapeutic molecules. In a preferred embodiment, the genetically modified bacteria are used in animals, including humans, birds, dogs, cattle and pigs, for protection against avian influenza and highly pathogenic derivatives.

Accordingly, when administered to an individual, a live *Salmonella* bacterial vaccine or therapeutic, in accordance with some embodiments of the present invention, that is genetically engineered to express one or more antigens or anti-parasitic molecules in combination with a protease inhibitor and have improved stability due to the presence of the protease inhibitor to elicit an immune response and or have direct anti-parasitic activity.

It is therefore an object to provide a genetically engineered bacterium for administration to an animal, having a genetically engineered construct that causes the bacterium to express a protease inhibitor. The protease sensitive molecule may comprise, for example, an antigen configured to raise an immune response in the animal, and/or a protease sensitive molecule, e.g., a therapeutic peptide. For example, the protease sensitive molecule may comprise an antiparasitic molecule.

An antigen produced may be configured to raise an immune response in the animal against the beta-amyloid peptide associated with Alzheimer's disease or the polyglutamine peptide (polyQ) associated with Huntington's disease.

The bacterium may co-express the protease inhibitor and a protease sensitive molecule. Alternately, a co-culture of bacteria which each express different constructs may be provided, or two different cultures provided. Preferably, the protease inhibitor and protease sensitive molecule are expressed within the same tissue, and preferably are present at lower concentrations outside of a targeted tissue or tissues.

According to one embodiment, the protease sensitive molecule comprises a viral antigen. The viral antigen may comprise an antigen which induces production of antibodies in the animal to influenza hemagglutinin or influenza neuraminidase. That is, the bacteria may produce a hemagglutinen or neuraminidase itself, a multimer, or subportion thereof. Likewise, the antigen may be a genetically engineered synthetic sequence that encodes a product which is distinct from a natural antigen, but shares common antigenic determinants and raises a desired immune response. The protease sensitive molecule may also comprise a protozoan antigen and/or a helminth antigen, for example. The antigen may be provided as a therapeutic agent representing a vaccination, or as an immunostimulant or adjuvant.

The protease sensitive molecule comprises, for example, an antigen associated with a parasite which colonizes or attaches to a mucosal or endothelial surface and/or an antigen associated with an infectious disease in which infectious disease particles are located near an animal mucosal surface.

The bacterium may comprise a *Salmonella* bacterium having an attenuating mutation a genetic locus selected from the group consisting of one or more of phoP−, phoQ−, edt−, cya−, crp−, poxA−, rpoS−, htrA−, nuoG−, pmi−, pabA, pts, damA−, pur−, purA−, purB−, purl−, purF−, zwf−, aroA−, aroB−, aroC−, aroD−, serC−, gua−, cadA−, rfc−, rjb−, rfa−, ompR−, msbB−, pfkAB−, crr−, glk−, ptsG−, ptsHI−, manXYZ−, Suwwan, trxA−, gor−, and DsbA+. Preferably, the bacterium comprises a *Salmonella* bacterium having attenuating mutations msbB−, Suwwan, zwf−, trxA− and gor−. Further, the bacterium may be genetically engineered to be conjugation deficient.

Another object provides a method of treating a disease in an animal, comprising: administering to the animal a pharmaceutically acceptable formulation, comprising a live genetically engineered bacterium that is adapted to express at least a protease inhibitor adapted to inhibit a protease; and permitting the live bacterium to grow within a tissue of the animal to produce in situ the protease inhibitor and inhibit a protease of the animal or an animal parasite. The bacterium may co-express a protease-sensitive therapeutic agent and the protease inhibitor within an affected tissue of the animal infected with a target organism. The bacterium may co-express the protease-sensitive therapeutic agent and the protease inhibitor directly within or proximate to a parasite of the animal. The bacterium may comprise a *Salmonella* bacterium having an attenuating mutation a genetic locus selected from the group consisting of one or more of phoP−, phoQ−, edt−, cya−, crp−, poxA−, rpoS−, htrA−, nuoG−, pmi−, pabA, pts, damA−, pur−, purA−, purB−, purl−, purF−, zwf−, aroA−, aroB−, aroC−, aroD−, serC−, gua−, cadA−, rfc−, rjb−, rfa−, ompR−, msbB−, pfkAB−, crr−, glk−, ptsG−, ptsHI−, manXYZ−, Suwwan, trxA−, gor−, and DsbA+.

A further object provides a pharmaceutically acceptable formulation suitable for therapeutic administration to an animal, comprising a genetically engineered bacterium having at least one genetic construct that controls the bacterium to express a protease inhibitor adapted to, and produced in sufficient quantity to, impede a degradation of an exogenous therapeutic protease sensitive molecule by a protease produced by the animal or an animal parasite, wherein an activity of the protease sensitive molecule portion is increased with respect to an absence of the protease inhibitor. The bacterium may comprise a *Salmonella* bacterium which co-expresses the exogenous therapeutic molecule, having an attenuating mutation a genetic locus selected from the group consisting of one or more of phoP−, phoQ−, edt−, cya−, crp−, poxA−, rpoS−, htrA−, nuoG−, pmi−, pabA, pts, damA−, pur−, purA−, purB−, purl−, purF−, zwf−, aroA−, aroB−, aroC−, aroD−, serC−, gua−, cadA−, rfc−, rjb−, rfa−, ompR−, msbB−, pfkAB−, crr−, glk−, ptsG−, ptsHI−, manXYZ−, Suwwan, trxA−, gor−, and DsbA+.

4. DEFINITIONS

In order that the description of the various aspects of the invention may be more fully understood, the following terms are defined.

As used herein, "attenuated", "attenuation", and similar terms refer to elimination or reduction of the natural virulence of a bacterium in a particular host organism, such as a mammal.

"Virulence" is the degree or ability of a pathogenic microorganism to produce disease in a host organism. A bacterium may be virulent for one species of host organism (e.g., a mouse) and not virulent for another species of host organism (e.g., a human). Hence, broadly, an "attenuated" bacterium or strain of bacteria is attenuated in virulence toward at least one species of host organism that is susceptible to infection and disease by a virulent form of the bacterium or strain of the bacterium.

As used herein, the term "genetic locus" is a broad term and comprises any designated site in the genome (the total genetic content of an organism) or in a particular nucleotide sequence of a chromosome or replicating nucleic acid molecule (e.g., a plasmid), including but not limited to a gene, nucleotide coding sequence (for a protein or RNA), operon, regulon, promoter, inducible promoters (including tetracycline, arabinose, (EP1,655,370 A1, expressly incorporated in its entirety herein), salicylic acid, hypoxic, tumor cell specific inducible promoters) regulatory site (including transcriptional terminator sites, ribosome binding sites, transcriptional inhibitor binding sites, transcriptional activator binding sites), origin of replication, intercistronic region, and portions therein. It is understood that all protein expression constructs require a stop signal. A genetic locus may be identified and characterized by any of a variety of in vivo and/or in vitro methods available in the art, including but not limited to, conjugation studies, crossover frequencies, transformation analysis, transfection analysis, restriction enzyme mapping protocols, nucleic acid hybridization analyses, polymerase chain reaction (PCR) protocols, nuclease protection assays, and direct nucleic acid sequence analysis The terms "oral", "enteral", "enterally", "orally", "non-parenteral", "non-parenterally", and the like, refer to administration of a compound or composition to an individual by a route or mode along the alimentary canal. Examples of "oral" routes of administration of a vaccine composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories that release a live bacterial vaccine strain described herein to the lower intestinal tract of the alimentary canal.

The term "recombinant" is used to describe non-naturally altered or manipulated nucleic acids, cells transformed, electroporated, or transfected with exogenous nucleic acids, and polypeptides expressed non-naturally, e.g., through manipulation of isolated nucleic acids and transformation of cells. The term "recombinant" specifically encompasses nucleic acid molecules that have been constructed, at least in part, in vitro using genetic engineering techniques, and use of the term "recombinant" as an adjective to describe a molecule, construct, vector, cell, polypeptide, or polynucleotide specifically excludes naturally existing forms of such molecules, constructs, vectors, cells, polypeptides, or polynucleotides.

Cassette, or expression cassette is used to describe a nucleic acid sequence comprising (i) a nucleotide sequence encoding a promoter, (ii) a first unique restriction enzyme cleavage site located 5' of the nucleotide sequence encoding the promoter, and (iii) a second unique restriction enzyme cleavage site located 3' of the nucleotide sequence encoding the promoter. The cassette may also contain a multiple cloning site (MCS) and transcriptional terminator within the 5' and 3' restriction endonuclease cleavage sites. The cassette may also contain cloned genes of interest.

As used herein, the term "*salmonella*" (plural, "salmonellae") and "*Salmonella*" refers to a bacterium that is a serovar of *Salmonella enterica*. A number of serovars of *S. enterica* are known. Particularly preferred *salmonella* bacteria useful in some embodiments of the invention are attenuated strains of *Salmonella enterica* serovar *Typhimurium* ("*S. typhimurium*") and serovar *Typhi* ("*S. typhi*") as described herein.

As used herein, the terms "strain" and "isolate" are synonymous and refer to a particular isolated bacterium and its genetically identical progeny. Actual examples of particular strains of bacteria developed or isolated by human effort are indicated herein by specific letter and numerical designations (e.g. strains Ty21a, CMV906, CMV908, CMV906-htr, CMV908-htr, Ty800, holavax, M01ZH09, VNP20009).

The definitions of other terms used herein are those understood and used by persons skilled in the art and/or will be evident to persons skilled in the art from usage in the text.

5. BRIEF DESCRIPTION OF THE DRAWINGS

Figure 2:
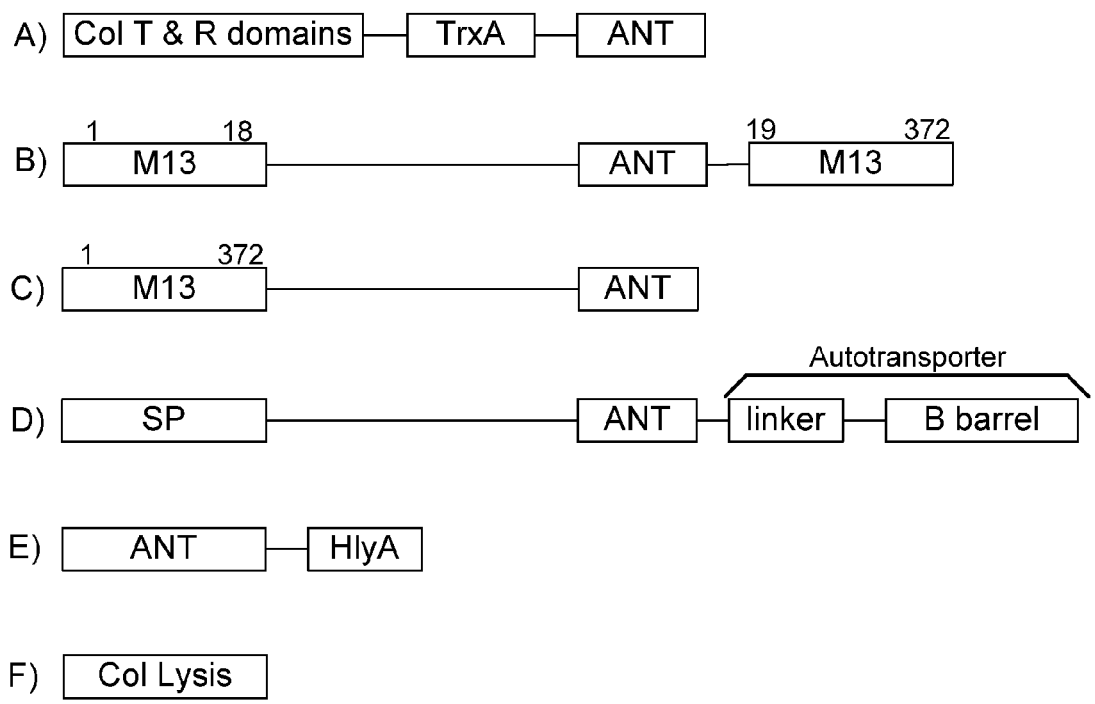
Figure 3:
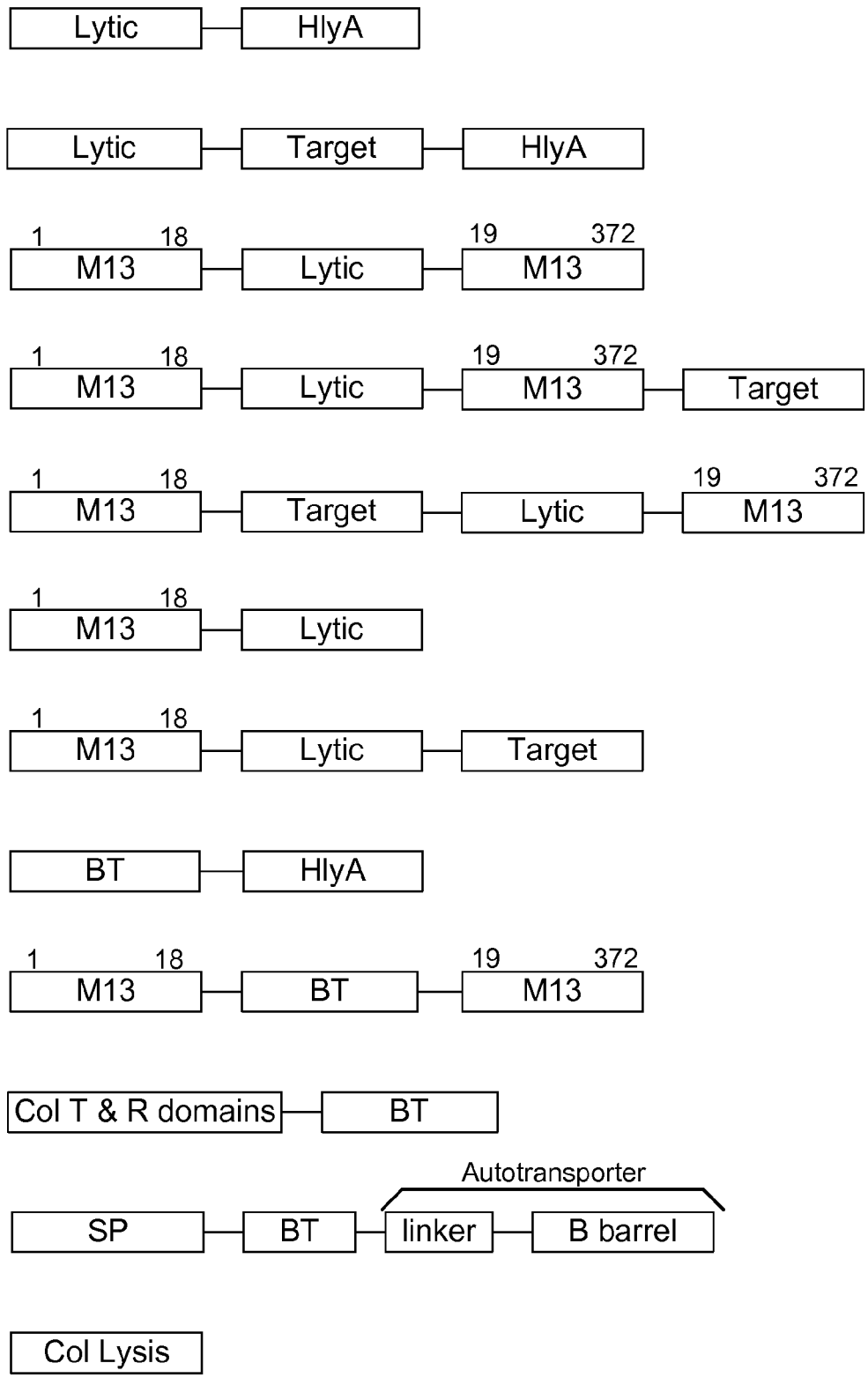

FIG. 1 shows chimeric secreted protease inhibitors.
FIG. 2 shows chimeric secreted antigens.
FIG. 3 shows chimeric secreted lytic and therapeutic peptides.

6. DETAILED DESCRIPTION OF THE INVENTION

The present invention provides, according to various embodiments, improved live attenuated therapeutic bacterial strains that express one or more therapeutic molecules together with one or more protease inhibitor polypeptides that inhibit local proteases that could deactivate the therapeutic molecules. In particular, one aspect of the invention relates to live attenuated bacterial strains that may include *Salmonella* vectoring novel chimeric antigens and/or anti-infective toxins to an individual to elicit a therapeutic response against an infectious disease. The types of infectious diseases may generally include prions, viruses, bacteria, protozoans (protists), fungi and helminthes (Mandell, Bennett and Dolin 2010, Principles and Practices of Infectious Diseases, 7$^{th}$ Edition, Elsiever Publishers, 4320 pages). Another aspect of the invention relates to reducing or eliminating the bacteria's ability to undergo conjugation, further limiting incoming and outgoing exchange of genetic material.

For reasons of clarity, the detailed description is divided into the following subsections: protease sensitivity; protease inhibitors; antigens, lytic peptides, anti-infective proteins, targeting ligands, limiting conjugation and characteristics of some embodiments of the invention.

6.1. Protease Sensitivity.

The therapeutic proteins of some embodiments of the invention, including protease inhibitors, antigens, lytic peptides and therapeutic peptides, may be sensitive to proteases that exist at the site of infection, or from or within the infectious agent itself (e.g., Wanyiri et al., Infect Immun. 2007 January; 75(1): 184-192). Proteases may be classified by several different systems, for example, into six groups: serine proteases, threonine proteases, cysteine proteases, aspartate proteases, metalloproteases and glutamic acid proteases. Alternatively, proteases may be classified by the optimal pH in which they are active: acid proteases, neutral proteases, and basic proteases (or alkaline proteases). Well known proteases of the gut include trypsin, chymotrypsin, pepsin, carboxypeptidases and elastases. Other proteases such as furin, plasmin and lysosomal proteases and cathepsins may also be present. The protease sensitive proteins may also have protease cleavage sites that are artificially added to the protein being expressed. Assay of protease sensitivity is known to those skilled in the art.

6.2. Protease Inhibitors

Protease inhibitors of some embodiments of the invention are preferably based on known or novel polypeptide inhibitors. The inhibitors include both synthetic peptides and naturally occurring, endogenous peptides. Classes of proteases are: cysteine protease inhibitors, serine protease inhibitors (serpins), trypsin inhibitors, Kunitz STI protease inhibitor, threonine protease inhibitors, aspartic protease inhibitors, metalloprotease inhibitors. Protease inhibitors can also be classified by mechanism of action as suicide inhibitors, transition state inhibitors, protein protease inhibitor (see serpins) and chelating agents. The protease inhibitors of some embodiments of the invention are protein or polypeptide inhibitors encoded by DNA contained within the bacteria.

To result in the desired activity, the protease inhibitor peptides should be released or secreted outside of the bacteria, or displayed on the bacterial surface. Accordingly, the protease inhibitory peptides are modified by fusing them to secretion signals or co-expressed with colicin or bacteriophage lytic proteins as shown in FIG. 1. The secretion signals may be either N-terminal (derived from colicins, LPP:OmpA, M13pIII) or C-terminal (last 60 amino acids of an RTX protein such as the *E. coli* HlyA hemolysin, together with the required HlyBD supplied in trans and endogenous tolC). The secretion system may also be the autotransporter system, resulting in either surface displayed or released protease inhibitor. The N-terminal signal sequences are well known and characterized by the presence of a signal sequence cleavage site for an endogenous bacterial protease. Release may be further affected by co-expression of a colicin release protein. Thus, N-terminal signal sequences provide protease inhibitors, free from the signal sequence. The C-terminal signal sequence may be further engineered to have a protease cleavage site in between the protease inhibitory peptide and the signal sequence, such as a trypsin cleaveage signal (FQNALLVR, SEQ ID NO:47). The cleavage site may be for the same protease that the peptide inactivates. Thus, the protease activates its own inhibitor. The protease cleavage site may also be for a protease other than for the protease inhibitor, thus deactivating another protease. Multiple protease inhibitor peptides may be used in-frame with multiple protease cleavage signals (polymeric protease activated protease inhibitors), where the inhibitors alternate with cleavage sites. The polymeric protease activated protease inhibitors can be homo- or hetero-inhibitor polymers (i.e., have inhibitors for the same or different proteases, respectively), and/or homo- or hetero-protease cleavage polymers (i.e., have the same or different protease cleavage sites). Assay of protease inhibitors is known to those skilled in the art.

Protease inhibitors have been reviewed by Laskowski and Kato, 1980, (Annual Review of Biochemistry 49: 593-626). Serine proteases inhibitors, the largest group, include 1) bovine pancreatic trypsin inhibitor (Kunitz) family, 2) pancreatic secretory trypsin inhibitor (Kazal) family, 3) *Streptomyces* subtilisin inhibitor family, 4) soybean trypsin inhibitor (Kunitz) family, 5) soybean proteinase inhibitor (Bowman-Birk) family 6) potato I inhibitor family, 7) potato II inhibitor family, 8) *Ascaris* trypsin inhibitor family, and 9) others. Protease inhibitors have also been grouped within the MEROPS peptidase database (Rawlings et al., 2008 Nucleic Acids Res. 36 Database issue, D320-325).

Specific examples of protease inhibitors that may be expressed as complete proteins or peptide fragments corresponding to the active inhibitory site include but are not limited to aprotinin, cathepsin inhibitor peptide sc-3130, *Neisseria* protease inhibitor, lymphocyte protease inhibitor, maspin, matrix metalloprotease inhibitors, macroglobulins, antithrombin, equistatin, Bowman-Birk inhibitor family, ovomucoid, ovoinhibitor-proteinase inhibitors from avian serum, dog submandibular inhibitors, inter-a-trypsin inhibitors from mammalian serum, chelonianin from turtle egg white, soybean trypsin inhibitor (Kunitz), secretory trypsin inhibitors (Kazal) $a_i$-proteinase inhibitor, *Streptomyces* subtilisin inhibitor, plasminostreptin, plasmin inhibitor, factor Xa inhibitor, coelenterate protease inhibitors, protease inhibitor anticoagulants, ixolaris, human Serpins (SerpinA1 (alpha 1-antitrypsin), SerpinA2, SerpinA3, SerpinA4, SerpinA5, SerpinA6, SerpinA7, SerpinA8, SerpinA9, SerpinA10, SerpinA11, SerpinA12, SerpinA13, SerpinB1, SerpinB2, SerpinB3, SerpinB4, SerpinB5, SerpinB6, SerpinB7, SerpinB8, SerpinC1 (antithrombin), SerpinD1, SerpinE1, SerpinE2, SerpinF1, SerpinF2, SerpinG1, SerpinNI1, SerpinNI2), cowpea trypsin inhibitor, onion trypsin inhibitor, alpha 1-antitrypsin, *Ascaris* trypsin and pepsin inhibitors, lipocalins, CI inhibitor, plasminogen-activator inhibitor, collegenase inhibitor, Acp62F from *Drosophila*, bombina trypsin inhibitor, *bombyx* subtilisin inhibitor, von Willebrand factor, leukocyte secretory protease inhibitor. Short peptide inhibitors of protease are preferred. Many protease inhibitors have one or more disulfide bonds. Fusion to thioredoxin (trxA) is known to improve protease inhibitor activity (e.g., Furuki et al., 2007, Fukuoka University Science Reports (Vol. 37, No. 1, Heisei 19 September) 37: 37-44). Fusion to glutathione-S transferase (GST) and co-expression with disulfide bond isomerase (DsbA) is also known to improve solubility. Examples of the peptide sequences of short peptide inhibitors are shown in Table 1.

TABLE 1

Sequences of short protease inhibitor peptides

| Protease Inhibitor | Protease(s) inhibited | Protein/Peptide Name and/or Peptide Sequence | |
|---|---|---|---|
| Leupeptin | calpain, plasmin, trypsin, papain, and cadicpsin B | Leupeptin | |
| Aprotinin | Trypsin Plasmin Tissue kallikrein | RPDFC LEPPY TGPCK ARIIR YFYNA KAGLC QTFVY GGCRA KRNNF KSAED CMRTC GGA | SEQ ID NO:1 |
| Aprotinin homologues | Variable | Brinkmann et al, 1991 Eur J. Biochem 202: 95-99 | |
| Protease Inhibitor 15 | Trypsin | Synthetic peptide: CFPGVTSNYLYWFK, SEQ ID NO: 48, corresponding to amino acids 245-258 of human protease inhibitor. | |
| Tissue protease inhibitor | Serine protease inhibitor, Kazal type 1, mature | DSLGREAKCYNELNGCTKIYDPVCGTDGNTYPNECVL CFENRKRQTSILIQKSGPC | SEQ ID NO:2 |
| Furin inhibitors | Furin | PAAATVTKKVAKSPKKAKAAKPKKAAKSAAKAVKPK | SEQ ID NO:3 |
| | | TKKVAKRPAKRAA | SEQ ID NO:4 |
| | | TKKVAKRPAKRDL | SEQ ID NO:5 |
| | | GKRPRAKRA | SEQ ID NO:6 |
| | | CKRPRAKRDL | SEQ ID NO:7 |
| | | CVAKRPRAKRDL | SEQ ID NO:8 |
| | | CKKVAKRPAKRDL | SEQ ID NO:9 |
| | | RRRRRR L6R (hexa-L-arginine) | SEQ ID NO:10 |
| Kallikrein Inhibitors | Kallikrein 2 | SRFKVWWAAG | SEQ ID NO:11 |
| | | AARRPFPAPS | SEQ ID NO:12 |
| | | PARRPFPVTA | SEQ ID NO:13 |
| Pepsinogen 1-16 | Pepsin | LVKVPLVRKKSLRQNL | SEQ ID NO:14 |
| | | Dunn et al., 1983 Biochem J 209: 355-362 | |
| Pepsinogen 1-12 | Pepsin | LVKVPLVRKKSL | SEQ ID NO:15 |
| | | Dunn et al., 1983 Biochem J 209: 355-362 | |
| Pepsinogen 1-12 4-7 substitution | Pepsin | LVKGGLVRKKSL (II) [Gly4,5] | SEQ ID NO:16 |
| | | LVKVPGGRKKSL (III) [Gly6,7] | SEQ ID NO:17 |
| | | LVKGGGGRKKSL (IV) [Gly4-7] | SEQ ID NO:18 |
| | | Dunn et al., 1983 Biochem J 209: 355-362 | |
| Sunflower trysin inhibitor SFTI-1 | Trypsin | GRCTKSIPPICFPD | SEQ ID NO:19 |
| Odorrana trypsin inhibitor | Trypsin | AVNIPFKVHFRCKAAFC | SEQ ID NO:20 |

TABLE 1-continued

Sequences of short protease inhibitor peptides

| Ascaris chymotrypsin elastase inhibitor | Chymtrypsin Elastase | GQESCGPNEV WTECTGCEMK CGPDENTPCP LMCRRPSCEC SPGRGMRRTN DGKCIPASQCP | SEQ ID NO:21 |
|---|---|---|---|
| Ascaris trypsin inhibitor | Trypsin | EAEKCBZZPG WTKGGCETCG CAQKIVPCTR ETKPNPQCPR KQCCIASAGF VRDAQGNCIK FEDCPK | SEQ ID NO:22 |
| Ascaris trypsin inhibitor | Trypsin | EAEKCTKPNE QWTKCGGCEG TCAQKIVPCT RECKPPRCEC IASAGFVRDA QGNCIKFEDC PK | SEQ ID NO:23 |
| Onion trypsin inhibitor | Trypsin | MKAALVIFLL IAMLGVLAAE AYPNLRQVVV TGDEEEGGCC DSCGSCDRRA PDLARCECRD VVTSCGPGCK RCEEADLDLN PPRYVCKDMS FHSCQTRCSI L | SEQ ID NO:24 |
| Barley chymotrypsin inhibitor 2 | Chymotrypsin | MSSMEKKPEGVNIGAGDRQNQKTEWPELVGKSVEEAK KVILQDK PAAQIIVLPVGTIVTMEYRIDRVRLFVDRL DNIAQVPRVG | SEQ ID NO:25 |

6.3 Antigens.

Construction of chimeric bacterial proteins is used to adapt protein antigens such that they are released, surfaced displayed and/or secreted as shown in FIG. 2 to provide therapeutic molecules that are effective in eliciting an immune response. The antigens useful in some embodiments of the invention are known or novel proteins derived from infectious diseases (Mandell, Bennett and Dolin 2010, Principles and Practices of Infectious Diseases, 7th Edition, Elsevier Publishers, 4320 pages), or from cancer, Alzheimer's or Huntington's disease. Numerous specific antigens resulting in some degree of protective immunity have been described, e.g., WO/2009/150433 Flower et al., Antigenic Composition, expressly incorporated in its entirety herein. Epidermal growth factor receptors (EGFR) are known cancer antigens, beta-amyloid protein is a known antigen of Alzheimer's, and polyglutamine (polyQ) is a known antigen of Huntington's. However, there remains need to devise new ways improve upon the immune response. The antigens are secreted by bacteria using known secretion systems such as HlyA or autotransporters, or the novel colicin and M13 hybrids described herein. The antigens are expressed by the bacteria as described below from DNA constructs contained within the bacteria sufficient to result in the expression as described, and results in an improved immune response. Assay of antigenic responses are known to those skilled in the art, and is briefly described below.

6.4 Lytic Peptides

As diagramed in FIG. 3, the antiparasitic proteins are expressed as fusions that are secreted, released or surface displayed. The activity of the antiparasitic proteins is improved by co-expression with one or more protease inhibitors. The desirability of combining protease inhibitors with lytic peptides has not previously been recognized as a means of both improving activity and specificity. Small lytic peptides (less than 50 amino acids) are used to construct chimeric proteins for more than one purpose. The chimeric proteins containing lytic peptides may be directly cytotoxic for parasites or infectious agents. In order to be cytotoxic they must be released, surface displayed and/or secreted (FIG. 3) and may be provided with cell specificity by the addition of a targeting ligand. Small lytic peptides have been proposed for use in the experimental treatment of parasites and infectious diseases. However, it is evident that most, if not all, of the commonly used small lytic peptides have strong antibacterial activity, and thus are not compatible with delivery by a bacterium (see Table 1 of Leschner and Hansel, 2004 Current Pharmaceutical Design 10: 2299-2310). Small lytic peptides useful in some embodiments of the invention are those derived from *Staphylococcus aureus*, *S. epidermidis* and related species, including the phenol-soluble modulin (PSM) peptides and delta-lysin (Wang et al., 2007 Nature Medicine 13: 1510-1514). The selection of the lytic peptide depends upon the primary purpose of the construct, which may be used in combination with other constructs providing other anticancer features. That is, the therapies provided in accordance with aspects of the present invention need not be provided in isolation, and the bacteria may be engineered to provide additional therapies or advantageous attributes. Constructs designed to be directly cytotoxic to cells employ the more cytoxic peptides, particularly PSM-alpha-3. Constructs which are designed to use the lytic peptide to affect escape from the endosome use the peptides with the lower level of cytotoxicity, such as PSM-alpha-1, PSM-alpha-2 or delta-lysin. Larger lytic peptides that may be used includes the actinoporins and equinatoxins from sea anemones or other coelenterates (Anderluh and Macek 2002, Toxicon 40: 111-124), are generally more potent than the bacterially-derived peptides, and are selected for use in being directly cytotoxic to parasites. Assay of lytic peptides is known to those skilled in the art.

TABLE 2

Membrane lytic peptides useful in some embodiments of the invention

| Peptide and source | Peptide Sequence | |
|---|---|---|
| Processed << short >> active delta lysin S aureus | MAQDIISTISDLVKWIIDTVN KFTKK | SEQ ID NO:26 |
| Delta lysin processed S epidermitidis | MMAADIISTI GDLVKWIIDTV NKFKK | SEQ ID NO:27 |
| Delta lysin from CA-MRSA | MAQDIISTISDLVKWIIDTVN KFTKK | SEQ ID NO:28 |
| PSM- alpha-1 | MGIIAGIIKVIKSLIEQFTGK | SEQ ID NO:29 |
| PSM-alpha-2 | MGIIAGIIKFIKGLIEKFTGK | SEQ ID NO:30 |
| PSM-alpha-3 | MEFVAKLFKFFKDLLGKFLGNN | SEQ ID NO:31 |
| PSM-alpha-4 | MAIVGTIIKIIKAIIDIFAK | SEQ ID NO:32 |
| PSM-beta-1 | MEGLFNAIKDTVTAAINNDGAK LGTSIVSIVENGVGLLGKLFGF | SEQ ID NO:33 |
| PSM-beta-2 | MTGLAEAIANTVQAAQQHDSVK LGTSIVDIVANGVGLLGKLFGF | SEQ ID NO:34 |
| Actinoporins Equinatoxins | Lytic peptides from sea anemones and other coelenterates | |

6.5 Anti-Infective Proteins

As diagramed in FIG. 3, the antiparasitic proteins are expressed as fusions that are secreted, released or surface displayed. It has been known that certain bacteria such as *Salmonella* are capable of infecting certain roundworms, such as *Caenorhabdities elegans* (Lavigne et al., 2008, PLoS ONE 3: e3370; Gereven et al., 2007, FEMS Micobiol Lett 278: 236-241). However, it has not been suggested nor has it been recognized as desirable to construct an attenuated bacterium such as a *Salmonella* that could directly infect roundworms or other parasites following oral ingestion. Nor has it been suggested to engineer any such bacterium to directly attack roundworms or other parasites and to deliver therapeutic proteins that inhibit or kill the parasite. Nor would it have been understood that the activity of the antiparasitic proteins is improved by co-expression with one or more protease inhibitors. Furthermore, the fact that parasites in the process of infection, may cause the release of proteases that might deactivate the bacterially secreted proteins of some embodiments of the invention. Proteins with antiparasite activity include bacterial toxins with anti-insect and/or anti-parasite activity, including those from *Bacillus thuringiensis* (e.g., BT toxin) which have potential for treating parasites and infectious diseases (see Li et al., 2008, Biological Control, 47: 97-102; Li, et al., 2007, Plant Biotechnology Journal 5:455-464; Cappello, M. (2006) Proc. Natl. Acad. Sci. 103(41): 15154-15159; Wei J. Z., 2003 Proc. Natl. Acad. Sci. 100: 2760-2765, U.S. Pat. No. 5,651,965 Payne, *Bacillus thuringiensis* toxins and genes active against nematodes). Secreted insecticidal toxins and phenol oxidase inhibitors including but not limited to stilbenes from *Photorhabdus* and *Xenorhabdus* species are also encompassed by some embodiments of the invention. Lectins with antiparasite activity such those proteins purified from the corms of *Pinellia ternata* and *Lycoris radiata*. Both *P. ternata* agglutinin (PTA) protein and *L. radiata* agglutinin (LRA) as are also encompassed (Gaofu et al., 2008, Journal of Invertebrate Pathology 98: 40-45). Other proteins and peptides with anti-infective activity include the anthelmintic cyclic heptapeptide segetalin D (Dahiya 2007, Acta Pol. Pharm. 64: 509-516) cyclodepsipeptids (Dutton et al., J. Med. Chem. 46: 2057-2073) phenylalanine rich peptides, and toxins containing tyrosine and aspartic acid repeats (YD repeats).

6.6 Targeting Peptides

As diagramed in FIG. 3, the anti-parasitic proteins are expressed as fusions that are secreted, released or surface displayed which may include targeting peptides. The activity of the anti-parasitic proteins with targeting peptides is improved by co-expression with one or more protease inhibitors. The targeting peptides are specific for the parasite to which the composition is directed. For example, phage display technology which is well known to those skilled in the art has been used to isolate peptides directed against *Plasmodium*, the causative agent of malaria (Lanzillotti et al., 2008, Trends In Parasitology 24: 18-23). Novel ligands may be isolated through standard phage display techniques (Barbass III et al., 2004, Phage Display, A Laboratory Manual, Cold Spring Harbor Press) including the use of commercially available kits (Ph.D-7 Phage Display Library Kit, New England Biolabs, Ipswich, Mass.). Thus for example, the peptide described by Li et al. (2008 Biochem Biophys Res Com 376: 489-493), ETTLKSF, SEQ ID NO:45, may be used as diagramed in FIG. 3 as an in-frame fusion for a bacterium directed toward malaria. Likewise, the peptide RGDS described by Quaissis et al. (1988 J. Protozool 35: 111-114) may be used as diagramed in FIG. 3 as an in-frame fusion for a bacterium directed toward leshmaniasis caused by *Leishmania* sp. Accordingly, known and novel peptides such as those determined through phage display to bind to a particular infectious agent are used in some embodiments of the invention.

6.7 Limiting Bacterial Conjugation

The fertility inhibition complex (finO and finP), are cloned onto the chromosome using standard genetic techniques such that strains either with or without an F' bacteria are not able to undergo bacterial conjugation. Other known inhibitory factors may also be used.

6.8 Characteristics of Therapeutic Bacteria Co-Expressing Protease Inhibitors with Chimeric Antigens, Lytic and Therapeutic Proteins The primary characteristic of the bacteria of certain embodiments of the invention is the enhanced effect of the effector molecule antigen, lytic peptide or anti-parasitic peptide relative to the parental strain of bacteria without expressing one or more protease inhibitors. In one embodiment, the percent increase in effect is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% greater than the parental strain of bacteria without expressing one or more protease inhibitors under the same conditions.

A secondary characteristic of the bacteria of some embodiments of the invention is that they carry novel chimeric proteins that improve their function compared to other chimeric protein expression systems. In one embodiment, the percent improvement is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% that of another expression system under the same conditions.

A third characteristic of the bacteria of some embodiments of the invention is that they carry novel chimeric proteins that prevent their elimination by antibodies compared to other chimeric protein expression systems. In one embodiment, the percent improvement is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% that of another expression system under the same conditions.

Overall improvement is defined as an increase in effect, such as the ability to kill a parasite in vitro by the bacteria, or the amount of an antibody produced in vivo following administration with the bacteria expressing an antigen, with and without the protease inhibitor, and/or with and without an antibody inhibiting peptide. The effect of the protease inhibitor on protein therapeutic activity is determined using standard techniques and assays known to those skilled in the art. Inhibitors are expressed as secreted proteins as described above. Likewise, the effect of the antibody inhibitory protein on therapeutic activity is determined using standard techniques and assays known to those skilled in the art. Antibody inhibitors are expressed as native proteins (e.g., IgA protease in gram negative bacteria for vectors such as those using *Salmonella*, or spa, IdeS and EndoS in gram positive bacteria for vectors such as those using *Streptococcus*) or as secreted protein chimeras as described above. The contribution of the therapeutic protein, protease inhibitors and/or antibody inhibitory proteins is determined individually and in combination. Additivity, synergy or antagonism may determined using the median effect analysis (Chou and Talaly 1981 Eur. J. Biochem. 115: 207-216) or other standard methods.

7. FIGURE LEGENDS

FIG. 1. Secreted Protease Inhibitors (PIs).

A) A PI followed by the hlyA C-terminal signal sequence.

B) A PI followed by an intervening protease cleavage site (downward arrow) and the hlyA C-terminal signal sequence.

B') Multiple protease inhibitor peptides may be used in-frame with multiple protease cleavage signals (polymeric protease activated protease inhibitors), where the inhibitors alternate with cleavage sites. The polymeric protease activated protease inhibitors can be homo- or hetero-inhibitor polymers (i.e., have multiple inhibitors for the same or different proteases, respectively), and/or homo- or hetero-protease cleavage polymers (i.e., have multiple of the same or different protease cleavage sites). Thus, protease inhibitors 1, 2 and 3 can be the same protease inhibitor or different protease inhibitors, and the protease cleavage sites (downward arrows) can be the same protease cleavage side or different protease cleavage sites.

C) A blocking peptide followed by an intervening protease cleavage site (downward arrow) and then the hlyA C-terminal signal sequence.

D) The LPP:OmpA signal sequence followed by a protease inhibitor.

E) The M13 pIII signal sequence (amino acids 1-18) followed by a protease inhibitor.

F) An autotransporter cassette consisting of an autotransporter signal peptide, a protease inhibitor (passenger) followed by the autotransporter linker and β-barrel.

G) A pINIIIompA leader with a protease inhibitor (Longstaff et al., Biochemistry 1990 29: 7339-7347).

H) A colicin N-terminal domain with a protease inhibitor.

I) A thioredoxin (TrxA) fusion with a PI followed by the hlyA C-terminal signal sequence.

J) A thioredoxin (TrxA) fusion with a PI followed by an intervening protease cleavage site (downward arrow) and the hlyA C-terminal signal sequence.

K) A blocking peptide followed by a thioredoxin (TrxA) fusion with an intervening protease cleavage site (downward arrow) and then the hlyA C-terminal signal sequence.

L) The LPP:OmpA signal sequence followed by a thioredoxin (TrxA) fusion with a protease inhibitor.

M) The M13 pIII signal sequence followed by a thioredoxin (TrxA) fusion with a protease inhibitor.

N) An autotransporter cassette consisting of an autotransporter signal peptide, a thioredoxin (TrxA) fusion and a protease inhibitor (passengers) followed by the autotransporter linker and β-barrel.

O) A pINIIIompA leader with a thioredoxin (TrxA) fusion with a protease inhibitor.

P) A colicin N-terminal domain with a thioredoxin (TrxA) fusion with a protease inhibitor. Q) F) A colicin lysis protein that may be co-expressed in trans with any of the above.

FIG. 2. Chimeric Antigens.

A) A colicin N-terminal domain fused in-frame with thioredoxin (TrxA) and an antigenic domain.

B) An M13 pIII signal sequence with amino acids 1 to 18 followed by an antigen and then a membrane anchor truncated M13 pIII amino acids 19 to 372.

C) An M13 pIII signal sequence with a membrane anchor truncated M13 pIII amino acids 1 to 372 and an antigen.

D) An autotransporter cassette consisting of an autotransporter signal peptide, an antigen (passenger) followed by the autotransporter linker and β-barrel.

E) An antigen fused to the 60 C-terminal amino acids of HlyA (together with HlyBD and tolC in trans).

F) A colicin lysis protein that may be co-expressed in trans with any of the above.

FIG. 3. Lytic and Therapeutic Peptide Chimeras.

A) A lytic peptide followed by the hlyA signal sequence.

B) A lytic peptide, parasite targeting (binding) peptide followed by an intervening protease cleavage site (downward arrow), hlyA signal peptide chimera.

C) The M13 pIII signal sequence followed by a lytic peptide and the membrane anchor truncated M13 pIII amino acids 19 to 372.

D) The M13 pIII signal sequence followed by a lytic peptide and the membrane anchor truncated M13 pIII amino acids 19 to 372 and a targeting peptide.

E) The M13 PIII signal sequence followed by a targeting peptide, a lytic peptide and the membrane anchor truncated M13 pIII amino acids 19-372.

F) The M13 pIII signal sequence followed by a lytic peptide.

G) The M13 pIII signal sequence followed by a lytic peptide.

H) A therapeutic peptide (e.g., BT toxin) fused to hlyA C-terminus.

I) The M13 pIII signal sequence followed by a therapeutic peptide and the membrane anchor truncated M13 pIII amino acids 19 to 372.

J) A colicin N-terminal domain followed by a therapeutic peptide.

K) An autotransporter cassette consisting of an autotransporter signal peptide, a therapeutic peptide (passenger) followed by the autotransporter linker and β-barrel.

L) A colicin lysis protein that may be co-expressed in trans with any of the above.

8. EXAMPLES

In order to more fully illustrate the invention, the following examples are provided.

8.1. Example

Methods for Obtaining Bacterial Strains with Suitable Genetic Backgrounds

A first step in selection of an appropriate strain based upon the known species specificity (e.g, *S. typhi* is human specific and *S. typhimurium* has broad species specificity including humans, birds, pigs and many other vertebrates). Thus, if the target species for immunization were limited to humans, *S. typhi* would be appropriate. If more species are desired to be immunized including humans, birds, pigs, cattle, dogs, horses and many other vertebrates, then other serotypes may be used. For example, *S. typhimurium* and *S. montevideo* which have non-overlapping O-antigen presentation (e.g., *S. typhimurium* is O-1, 4, 5, 12 and *S. typhi* is Vi, *S. montevideo* is O-6, 7) are representative examples. Methods to genetically alter the serotype within a single strain are known to those skilled in the art, including Favre et al., 1997 WO 97/14782 Methods for delivering heterologous O-antigens; and Roland, 2000, WO/2000/004919). Thus, *S. typhimurium* is a suitable serotype for a prime/boost strategy where *S. typhimurium* is either the primary vaccine, or the booster vaccine where the primary vaccine is another serotype such as *S. typhi* or *S. montevideo*. Furthermore, both *S. typhimurium* and *S. montevideo* are suitable for humans, pigs, cattle or birds. A second step follows serotype selection where the first genetic mutation is introduced which may involve the use of antibiotic resistance markers and where any antibiotic resistance makers are then eliminated, followed by a third step where a second genetic mutation is introduced which may involve the use of antibiotic resistance markers and where any antibiotic resistance makers are then also eliminated. Reiteration of genetic deletion and antibiotic marker elimination can be used to supply additional mutations. Methods for reiterative chromosomal deletion and elimination of antibiotic resistance markers are known to those skilled in the art, including TN10 transposon deletion followed by "Bochner" selection (Bochner et al., 1980, J. Bacteriol. 143: 926-933) for elimination of the tetracycline antibiotic resistance marker, lamda red recombinase deletion followed by flip recombinase elimination of the antibiotic resistance marker (Lesic and Rahme, 2008, BMC Molecular Biology 9:20), and suicide vectors such as those containing sucrase gene (e.g., pCVD442, Donnenberg and Kaper, 1991 Infect Immun 59: 4310-4317). Spontaneous mutations may also be rapidly and accurately selected for, such as the "Suwwan", a large IS200-mediated deletion (Murray et al., 2004, Journal of Bacteriology, 186: 8516-8523). Thus, the starting strain can be a wild type *Salmonella* such as ATCC 14028, and the Suwwan, IS200 deletion selected for using chlorate (Murray et al., 2004, Journal of Bacteriology, 186: 8516-8523). A second mutation in msbB can be introduced using pCVD442 as described by Low et al., 2004, Methods Mol. Med. 2004; 90:47-60). A third mutation can be generated in zwf as described by Karsten et al., 2009, BMC Microbiol. BMC Microbiol. 2009 Aug. 18; 9:170. Thus, the strain generated has deletions in the Suwwan region, msbB and zwf. In *S. montevideo*, where the Suwwan mutation is not known to occur, a pCVD442 vector is used to generate the equivalent mutation, together with the same procedures above (altered as necessary for DNA sequence variations in the DNA portions used for homologous recombination), resulting in a pair of strains having the same mutational background together with different bacterial antigens. These strains, alone or used for alternating doses, form a basic platform into which the antigens and protease inhibitor gene constructs are inserted.

8.2 Example

Production of Antigen Chimeras

Chimeric antigens are generated using standard molecular genetic techniques, including synthetic biology (e.g., chemically synthesized oligonucleotides annealed into larger constructs forming entire genes based on the nucleic acid and/or amino acid sequence selected) and expressed in bacteria using methods known to those skilled in the art, operably linking a promoter, ribosomal binding site and initiating methionine if not provided by the first portion of the construct. The construct may either be an exogenous plasmid or a chromosomal or virulence (VIR) plasmid integration vector, for which many different integration sites exist, including but not limited to any of the attenuation mutations or any defective (incomplete) phage elements, intergenic regions or the IS200 elements. The constructs may also be polycistronic, having multiple genes and/or gene products separated by ribosomal binding sites. The downstream region may contain a termination signal (terminator). Antigen fusions are performed in-frame. Any infectious disease for which an antigenic determinant is known may be used, as exemplified in FIG. 2A. For example, if a vaccine for influenza is needed, A colicin N-terminal domain, such as amino acids 1-232 of colE3: (MSGGDGRGHNTGAHSTSGNINGGPT-GLGVGGGASDGSGWSSENNPWGGGSGSGIHW GGGSGHGNGGGNGNSGGGSGTGGNL-SAVAAPVAFGFPALSTPGAGGLAVSISAGALSA AIADI-MAALKGPFKFGLWGVALYGVLPSQIAKD-DPNMMSKIVTSLPADDITESPVSSLPL DKATVNVNVRVVDDVKDERQNISVVS-GVPMSVPVVDAKPTERPGVFTASIPGAPVLNI) SEQ ID NO:35, is synthesized in frame with an antigen, such as the hemagglutinin from the H1N1 swine flu. The protein sequence for a portion of the swine flu hemagglutin, the HA1 fragment containing an initiating methionine and artificial second codon but without the initial signal sequence, an altered protease cleavage site and membrane anchor truncation (e.g., general antigen organization as described by Wei et al., 2008 J. Virology 82: 6200-6208) is given by the amino acid sequence:
MATFATANADTLCIGYHANNSTDTVDTV-LEKNVTVTHSVNLLEDKHNGKL CKLRGVA-PLHLGKCNIAGWILGNPECESLSTASS-WSYIVETSSSDNGTCY PGDFIDYEELREQLSSVSSFERFEIFP-KTSSWPNHDSNKGVTAACPHAGA KSFYKNLI-WLVKKGNSYPKLSKSYINDKGKEVLVL-WGIHHPSTSADQQSL YQNADAYVFVGSSRYSKKFKPEIAIRP-KVRDQEGRMNYYWTLVEPGDKIT FEATGNLV-VPRYAFAMERNAGSGIIISDTPVHDCNT-TCQTPKGAINTSLP FQNIHPITIGKCPKYVKSTKLRLATGL-RNVPSIQSTGLFGAIAGFIEGGW TGMVDGWYGYH-HQNEQGSGYAADLKSTQNAIDEIT-NKVNSVIEKMNTQFT AVGKEFNHLEKRIENLNKKVDDGFLDIW-TYNAELLVLLENERTLDYHDSN VKNLYEKVR-SQLKNNAKEIGNGCFEFYHKCDNTCMES-VKNGTYDYPKYSE EAKLNREEIDG
SEQ ID NO:36

A colicin release protein, such as that of colE3 (MKKIT-GIILLLLAVIILSACQANYIRDVQG-GTVSPSSTAEVTGLATQ, SEQ ID NO:37) is expressed in trans in order to enhance secretion and/or release. Each of the genes may be localized to an exogenously introduced plasmid, the endogenous virulence (VIR) plasmid, or the chromosome, together as a polycistronic construct or separately as monocistronic constructs, within any of the deleted attenuating genes, IS200s, or intervening sequences as described for the functional insertion of the cytosine deaminase gene with an msbB deletion (King et al., 2009 Methods Mol. Biol. 542: 649-59; Nemunaitis et al., 2003, Cancer Gene Therapy 10: 737-744). Bacteria expressing any of these constructs are tested for secretion into the media by the ability of an antibody to the bona fide antigen to react with the proteins of the supernatant using a standard immunological assay such as an immunoblot or enzyme linked immunosorbent assay (ELISA).

8.3. Example

Selecting Protease Inhibitors

Protease inhibitors are generated using knowledge of the predicted proteolytic cleavage of the antigen or other effector molecule. For example, the ExPASy PeptideCutter tool: Gasteiger et al. (Protein Identification and Analysis Tools on the ExPASy Server, In: John M. Walker (ed): The Proteomics Protocols Handbook, Humana Press, 2005) may be used to test the predicted proteolytic sensitivity of the antigen or other effector molecule. Using ExPASy, the hemagglutinin in the example above would be cleaved extensively by chymotrypsin (between 46 to 98 times depending on high specificity FYW not before P (46 times) or low specificity FYWML (SEQ ID NO:50) not before P (98 times), while there are no Factor Xa sites. Thus, since cleavage of the effector molecule has the potential to occur, chymotrypsin represent a protease target for which inhibition would improve the antigenicity or activity of a co-expressed molecule by inhibiting its destruction by proteolytic degradation, whereas Factor Xa is identified as a cleavage site that is not present, does not need to be inhibited, and who's cleavage recognition site could be added between protein domains where removal of a domain by proteolysis is desirable.

8.4. Example

Secreted Protease Inhibitors

Secreted protease inhibitors are generated using standard molecular genetic techniques and expressed in bacteria using methods known to those skilled in the art, operably linking a promoter, ribosomal binding site and initiating methionine if not provided by the first portion of the construct. The construct may either be a plasmid or a chromosomal integration vector, for which many different integration sites exist, including but not limited to any of the attenuation mutations or any of the IS200 elements. The constructs may also be polycistronic, having multiple genes and/or gene products separated by ribosomal binding sites. The downstream region may contain a termination signal (terminator). Different forms of the protease inhibitor constructs are shown in FIG. 1. The constructs used have multiple forms, such as: FIG. 1A) a protease inhibitor such as the *Ascaris* chymotrypsin and elastase inhibitor GQESCGPNEV WTECTGCEMK CGPDENTPCP LMCRRPSCEC SPGRGMRRTN DGKCIPASQCP SEQ ID NO:38 followed by the C-terminal signal sequence of hlyA STYGSQDYLNPLINEISKIISAAGNLDVKEERSAASLLQLSGNASDFSYGRNSITLTASA, SEQ ID NO:39 or FIG. 1B) a protease inhibitor such as the *Ascaris* chymotrypsin and elastase inhibitor GQESCGPNEV WTECTGCEMK CGPDENTPCP LMCRRPSCEC SPGRGMRRTN DGKCIPASQCP, SEQ ID NO:40 followed by a factor Xa cleavage site (IEGR↓, SEQ ID NO:49) followed by the C-terminal signal sequence of hlyA STYGSQDYLNPLINEISKIISAAGNLDVKEERSAASLLQLSGNASDFSYGRNSITLTASA, SEQ ID NO:41, or FIG. 1E) An N-terminal signal sequence, such as that from M13 pIII (MKKLLFAIPLVVPFYSHS SEQ ID NO:42), followed by a protease inhibitor such as the *Ascaris* chymotrypsin and elastase inhibitor GQESCGPNEV WTECTGCEMK CGPDENTPCP LMCRRPSCEC SPGRGMRRTN DGKCIPASQCP, SEQ ID NO:43. Several other secreted protease inhibitor forms are diagramed in FIG. 1, including the use of an autotransporter system and fusion with thioredoxin (trxA). A colicin release protein, such as that of colE3 (MKKITGIILLLLAVIILSACQANYIRDVQGGTVSPSSTAEVTGLATQ, SEQ ID NO:44) may be expressed in trans in order to enhance secretion and/or release. Bacteria expressing any of these constructs are tested for secretion into the media and the ability of the media to inhibit a protease such as chymotrypsin in a standard protease assay known to those skilled in the art. Many protease assays are commercially available, such as the QuantiCleave Fluorescent Protease Assay Kit, and QuantiCleave Protease Assay Kit II (Thermo/Fisher, Rockford, Ill.), Protease Assay Kit (G Biosciences, Maryland Heights, Mo.), PepTag Protease Assay (Promega, Madison, Wis.; 1993 Promega Notes Magazine 44: 2), Viral Protease Assay Kits (AnaSpec, Fremont, Calif.), Protease Assay Kit from Calbiochem (Calbiochem, San Diego, Calif.). Standard laboratory techniques to measure protease activity, and thus the reduced activity of protease inhibitors, include densitometric, spectrophotometric, colorometric and fluorometric assays, sodium dodecyl sulfate (SDS) polyacrylamide gel electrophoresis (PAGE), two dimensional SDS-PAGE, high pressure liquid chromatography (HPLC) and mass spectroscopy (mass-spec).

8.5. Example

Determining Immune Response to an Influenza Hemagglutinin-Expressing Bacteria

Experimental determination of vaccine activity is known to those skilled in the art. By way of non-limiting example, determination of an antibody response is demonstrated. It is understood that the resulting bacteria are then determined for $LD_{50}$ using standard methods (e.g., Welkos and O'Brien, 1994, Determination of median lethal and infectious doses in animal model systems, Meth. Enzymol. 235: 29-39) in order that the experiments proceed using safe doses. Translation to human studies is performed using multiples species (e.g., dogs, monkeys, pigs) and that a safe does is chosen well below the safe does in other species on either a mg/kg or mg/meter square.

1) Vertebrate animals including mice, birds, dogs, cats, horses, pigs or humans are selected for not having any known current or recent (within 1 year) influenza infection or vaccination. Said animals are pre-bled to determine background binding to, for example, hemagglutinin antigens.

2) The *Salmonella* expressing hemagglutinin are cultured on LB agar overnight at 37°. Bacteria expressing the antigens in combination with a protease inhibitor may also be used.

3) The following day the bacteria are transferred to LB broth, adjusted in concentration to $OD_{600}$=0.1 (~$2 \times 10^8$ cfu/ml), and subjected to further growth at 37° on a rotator to $OD_{600}$=2.0, and placed on ice, where the concentration corresponds to approx. $4 \times 10^9$ cfu/ml.

4) Following growth, centrifuged and resuspended in 1/10 the original volume in a pharmacologically suitable buffer such as PBS and they are diluted to a concentration of $10^4$ to $10^9$ c.f.u./ml in a pharmacologically suitable buffer on ice, warmed to room temperature and administered orally or parenterally in a volume appropriate for the size of the animal in question, for example 50 μl for a mouse or 10 to 100 ml for a human by oral administration. The actual dose measured in total cfu is determined by the safe dose as described above.

5) After 2 weeks, a blood sample is taken for comparison to the pretreatment sample. A booster dose may be given. The booster may be the same serotype and containing the same antigens (and/or protease inhibitors) as the initial administration, a different species, a different serotype, or a different flagellar antigen (H1 or H2) or no flagellar antigen.

6) After an additional 2 to 4 weeks, an additional blood sample may be taken for further comparison with the pretreatment and 2 week post treatment.

7) A comparison of preimmune and post immune antibody response is preformed by immunoblot or ELISA. A positive response is indicated 1) by a relative numerical value 20% or greater than background/preimmune assay with the antigen alone, and/or 2) by a relative numerical value 20% or greater than without the protease inhibitor.

8.6. Example

Immunization with a Hemagglutinin-Expressing Bacterial Vaccine Strains

An experiment to determine if hemagglutinin-expressing strains of *Salmonella* are capable of providing protection from challenge with the wildtype strain with improvement from co-expression with protease inhibitors. Ducks are immunized orally with a tolerated dose of bacteria when 4 weeks old, then challenged with the standard challenge model of influenza at 6 weeks age.

Birds in Group A are immunized with empty vector. Group B receive *Salmonella* expressing hemagglutinin. Group C is immunized with *Salmonella* expressing the protease inhibitor with no antigen. Group D is immunized with *Salmonella* expressing the hemagglutinin antigen and the protease inhibitor. Birds in Group E are not immunized. Comparative results of these experiments can be used to demonstrate the effectiveness of the vaccine with and without protease inhibitor.

8.7 Example

Therapeutic Peptides with Lytic Anti-Parasite Activity

Therapeutic peptides are generated using standard molecular genetic techniques and expressed in bacteria using methods known to those skilled in the art, operably linking a promoter, ribosomal binding site and initiating methionine if not provided by the first portion of the construct. The construct may either be a plasmid or a chromosomal integration vector, for which many different integration sites exist, including but not limited to any of the attenuation mutations or any of the IS200 elements. The constructs may also be polycistronic, having multiple genes and/or gene products separated by ribosomal binding sites. The downstream region may contain a termination signal (terminator). Antigen fusions are performed in-frame. An example of an antigen fusion is given in FIG. 3B. The lytic peptide PSM-alpha-3 MEFVAKLFKFFKDLLGKFLGNN, SEQ ID NO:31 is fused to the malaria targeting peptide ETTLKSF, SEQ ID NO:45, followed by a factor Xa cleavage site (IEGR↓, SEQ ID NO:49) C-terminal signal sequence of hlyA STYG-SQDYLNPLINEISKIISAAGNLDVKEER-SAASLLQLSGNASDFSYGRNSITLTASA SEQ ID NO:46. A colicin release protein, such as that of colE3 may be expressed in trans in order to enhance secretion and/or release. Bacteria expressing any of these constructs are tested for secretion into the media by the ability of the media to kill a parasite, such as *Plasmodium* sp., the causative agents of malaria.

It will be understood that the foregoing is only illustrative of the principles of the invention, and that various modifications can be made by those skilled in the art without departing from the scope and spirit of the invention.

---

What is claimed is:

1. A genetically engineered bacterium being attenuated and pharmaceutically acceptable as a non-lethal effective therapy for administration to an animal, and, having at least one first genetically engineered construct that both encodes for, and causes the bacterium to express and secrete within the animal a gene product comprising a protease inhibitor which is heterologous with respect to bacteria and configured to inhibit the at least one eukaryotic protease, wherein the genetically engineered bacterium has at least one second genetically engineered construct that both encodes for, and causes the bacterium to express a protease sensitive molecule which is heterologous with respect to bacteria, susceptible to degradation by the at least one eukaryotic protease produced by the animal which is inhibited by the protease inhibitor.

2. The bacterium according to claim 1, wherein the protease sensitive molecule comprises an antigen configured to raise an immune response in the animal against the polyglutamine peptide associated with Huntington's disease.

3. The bacterium according to claim 1, wherein the protease sensitive molecule comprises an antineoplastic molecule.

4. The bacterium according to claim 1, wherein the protease sensitive molecule comprises an antigen configured to raise an immune response in the animal against the beta-amyloid peptide associated with Alzheimer's disease.

5. The bacterium according to claim 1, wherein the protease sensitive molecule comprises a viral antigen.

6. The bacterium according to claim 5, wherein the viral antigen comprises an antigen which induces production of antibodies in the animal to influenza hemagglutinin or influenza neuraminidase.

7. The bacterium according to claim 1, wherein the protease sensitive molecule comprises a protozoan antigen.

8. The bacterium according to claim 1, wherein the protease sensitive molecule comprises a helminth antigen.

9. The bacterium according to claim 1, wherein the protease sensitive molecule comprises an antigen associated with a tumor whose origin is a mucosal or endothelial surface.

10. The bacterium according to claim 1, wherein the protease sensitive molecule comprises an antigen associated with a neoplastic disease.

11. The bacterium according to claim 1, wherein the bacterium is a *Salmonella* bacterium having an attenuating mutation a genetic locus selected from the group consisting of one or more of phoP−, phoQ−, edt−, cya−, crp−, poxA−, rpoS−, htrA−, nuoG−, pmi−, pabA, pts, damA−, pur−, purA−, purB−, purI−, purF−, zwf−, aroA−, aroB−, aroC−, aroD−, serC−, gua−, cadA−, rfc−, rjb−, rfa−, ompR−, msbB−, pfkAB−, crr−, glk−, ptsG−, ptsHI−, manXYZ−, Suwwan, trxA−, gor−, and DsbA+.

12. The bacterium according to claim 1, wherein the bacterium comprises a *Salmonella* bacterium having attenuating mutations msbB−, Suwwan, zwf−, trxA− and gor−.

13. The bacterium according to claim 1, wherein the bacterium is genetically engineered to be conjugation deficient.

14. A method of treating a disease in an animal, comprising:
  i) administering to the animal a pharmaceutically acceptable formulation comprising a live genetically engineered bacterium having at least one first genetically engineered construct that both encodes for, and causes the bacterium to express and secrete within the animal a gene product comprising a protease inhibitor which is heterologous with respect to bacteria and configured to inhibit the at least one eukaryotic protease, wherein the genetically engineered bacterium has at least one second genetically engineered construct that both encodes for, and causes the bacterium to express a protease sensitive molecule which is heterologous with respect to bacteria, susceptible to degradation by the at least one eukaryotic protease produced by the animal which is inhibited by the protease inhibitor; and
  ii) permitting the live bacterium to grow within a tissue of the animal to produce in situ the protease inhibitor and inhibit a protease of the animal or an animal parasite.

15. The method according to claim 14, wherein the bacterium co-expresses a protease-sensitive therapeutic agent and the protease inhibitor within an affected tissue of the animal infected with a target organism.

16. The method according to claim 14, wherein the bacterium co-expresses the protease-sensitive therapeutic agent and the protease inhibitor directly within or proximate to a parasite of the animal.

17. The method according to claim 14, wherein the bacterium comprises a *Salmonella* bacterium having an attenuating mutation a genetic locus selected from the group consisting of one or more of phoP−, phoQ−, edt−, cya−, crp−, poxA−, rpoS−, htrA−, nuoG−, pmi−, pabA, pts, damA−, pur−, purA−, purB−, purI−, purF−, zwf−, aroA−, aroB−, aroC−, aroD−, serC−, gua−, cadA−, rfc−, rjb−, rfa−, ompR−, msbB−, pfkAB−, crr−, glk−, ptsG−, ptsHI−, manXYZ−, Suwwan, trxA−, gor−, and DsbA+.

18. A pharmaceutically acceptable formulation suitable for administration to an animal as a pharmaceutically acceptable therapy, comprising a genetically engineered attenuated bacterium having at least one first genetic construct that causes the bacterium to express a protease inhibitor encoded by the at least one first genetic construct which is heterologous with respect to bacteria, adapted to, and produced in sufficient quantity to, impede degradation by a protease produced by the animal or an animal parasite of a therapeutic protease sensitive molecule encoded by at least one second genetic construct which is heterologous with respect to bacteria and expressed by the genetically engineered attenuated bacterium, wherein a level of the protease sensitive molecule in a tissue of the animal or the animal parasite is increased with respect to an absence of the protease inhibitor as a result of at least reduced degradation of the protease sensitive molecule resulting from inhibition of the protease produced by the animal or the animal parasite by the protease inhibitor.

19. The pharmaceutically acceptable formulation according to claim 18, wherein the bacterium is a *Salmonella* bacterium which co-expresses the exogenous therapeutic molecule, having an attenuating mutation a genetic locus selected from the group consisting of one or more of phoP−, phoQ−, edt−, cya−, crp−, poxA−, rpoS−, htrA−, nuoG−, pmi−, pabA, pts, damA−, pur−, purA−, purB−, purI−, purF−, zwf−, aroA−, aroB−, aroC−, aroD−, serC−, gua−, cadA−, rfc−, rjb−, rfa−, ompR−, msbB−, pfkAB−, crr−, glk−, ptsG−, ptsHI−, manXYZ−, Suwwan, trxA−, gor−, and DsbA+.

* * * * *

SEQUENCE LISTING

```
<160> NUMBER OF SEQ ID NOS: 51

<210> SEQ ID NO 1
<211> LENGTH: 58
<212> TYPE: PRT
<213> ORGANISM: Artificial Sequence
<220> FEATURE:
<223> OTHER INFORMATION: Aprotinin

<400> SEQUENCE: 1

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 2
<211> LENGTH: 56
<212> TYPE: PRT
<213> ORGANISM: Artificial Sequence
<220> FEATURE:
<223> OTHER INFORMATION: Tissue Protease Inhibitor, Serine protease
      inhibitor, Kazal type 1, mature

<400> SEQUENCE: 2

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
        35                  40                  45
```

```
Leu Ile Gln Lys Ser Gly Pro Cys
    50              55

<210> SEQ ID NO 3
<211> LENGTH: 36
<212> TYPE: PRT
<213> ORGANISM: Artificial Sequence
<220> FEATURE:
<223> OTHER INFORMATION: Furin Inhibitor

<400> SEQUENCE: 3

Pro Ala Ala Ala Thr Val Thr Lys Lys Val Ala Lys Ser Pro Lys Lys
1               5                   10                  15

Ala Lys Ala Ala Lys Pro Lys Lys Ala Ala Lys Ser Ala Ala Lys Ala
            20                  25                  30

Val Lys Pro Lys
        35

<210> SEQ ID NO 4
<211> LENGTH: 14
<212> TYPE: PRT
<213> ORGANISM: Artificial Sequence
<220> FEATURE:
<223> OTHER INFORMATION: Furin Inhibitor

<400> SEQUENCE: 4

Thr Lys Lys Val Ala Lys Arg Pro Arg Ala Lys Arg Ala Ala
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Furin Inhibitor

<400> SEQUENCE: 5

Thr Lys Lys Val Ala Lys Arg Pro Arg Ala Lys Arg Asp Leu
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Furin inhibitor

<400> SEQUENCE: 6

Gly Lys Arg Pro Arg Ala Lys Arg Ala
1               5

<210> SEQ ID NO 7
<211> LENGTH: 10
<212> TYPE: PRT
<213> ORGANISM: Artificial Sequence
<220> FEATURE:
<223> OTHER INFORMATION: Furin inhibitor

<400> SEQUENCE: 7

Cys Lys Arg Pro Arg Ala Lys Arg Asp Leu
1               5                   10

<210> SEQ ID NO 8
<211> LENGTH: 12
<212> TYPE: PRT
```

```
<213> ORGANISM: Artificial Sequence
<220> FEATURE:
<223> OTHER INFORMATION: Furin inhibitor

<400> SEQUENCE: 8

Cys Val Ala Lys Arg Pro Arg Ala Lys Arg Asp Leu
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Furin inhibitor

<400> SEQUENCE: 9

Cys Lys Lys Val Ala Lys Arg Pro Arg Ala Lys Arg Asp Leu
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Furin inhibitor, hexa-arginine (L6R)

<400> SEQUENCE: 10

Arg Arg Arg Arg Arg Arg
1               5

<210> SEQ ID NO 11
<211> LENGTH: 10
<212> TYPE: PRT
<213> ORGANISM: Artificial Sequence
<220> FEATURE:
<223> OTHER INFORMATION: Kallikrein 2 Inhibitor

<400> SEQUENCE: 11

Ser Arg Phe Lys Val Trp Trp Ala Ala Gly
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Kallikrein 2 Inhibitor

<400> SEQUENCE: 12

Ala Ala Arg Arg Pro Phe Pro Ala Pro Ser
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Kallikrein 2 Inhibitor

<400> SEQUENCE: 13

Pro Ala Arg Arg Pro Phe Pro Val Thr Ala
1               5                   10

<210> SEQ ID NO 14
<211> LENGTH: 16
<212> TYPE: PRT
<213> ORGANISM: Artificial Sequence
```

```
<220> FEATURE:
<223> OTHER INFORMATION: Pepsinogen 1-16

<400> SEQUENCE: 14

Leu Val Lys Val Pro Leu Val Arg Lys Lys Ser Leu Arg Gln Asn Leu
1               5                   10                  15

<210> SEQ ID NO 15
<211> LENGTH: 12
<212> TYPE: PRT
<213> ORGANISM: Artificial Sequence
<220> FEATURE:
<223> OTHER INFORMATION: Pepsinogen 1-12

<400> SEQUENCE: 15

Leu Val Lys Val Pro Leu Val Arg Lys Lys Ser Leu
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Pepsinogen 1-12 4-7 substitution (II) [Gly4,5]

<400> SEQUENCE: 16

Leu Val Lys Gly Gly Leu Val Arg Lys Lys Ser Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Pepsinogen 1-12 4-7 substitution, (III)
      [Gly6,7]

<400> SEQUENCE: 17

Leu Val Lys Val Pro Gly Gly Arg Lys Lys Ser Leu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Pepsinogen 1-12 4-7 substitution, (IV) [Gly4-7]

<400> SEQUENCE: 18

Leu Val Lys Gly Gly Gly Gly Arg Lys Lys Ser Leu
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Sunflower trysin inhibitor SFTI-1

<400> SEQUENCE: 19

Gly Arg Cys Thr Lys Ser Ile Pro Pro Ile Cys Phe Pro Asp
1               5                   10

<210> SEQ ID NO 20
<211> LENGTH: 17
<212> TYPE: PRT
<213> ORGANISM: Artificial Sequence
```

```
<220> FEATURE:
<223> OTHER INFORMATION: Odorrana trypsin inhibitor

<400> SEQUENCE: 20

Ala Val Asn Ile Pro Phe Lys Val His Phe Arg Cys Lys Ala Ala Phe
1               5                   10                  15

Cys

<210> SEQ ID NO 21
<211> LENGTH: 61
<212> TYPE: PRT
<213> ORGANISM: Artificial Sequence
<220> FEATURE:
<223> OTHER INFORMATION: Ascaris chymotrypsin elastase inhibitor

<400> SEQUENCE: 21

Gly Gln Glu Ser Cys Gly Pro Asn Glu Val Trp Thr Glu Cys Thr Gly
1               5                   10                  15

Cys Glu Met Lys Cys Gly Pro Asp Glu Asn Thr Pro Cys Pro Leu Met
            20                  25                  30

Cys Arg Arg Pro Ser Cys Glu Cys Ser Pro Gly Arg Gly Met Arg Arg
        35                  40                  45

Thr Asn Asp Gly Lys Cys Ile Pro Ala Ser Gln Cys Pro
    50                  55                  60

<210> SEQ ID NO 22
<211> LENGTH: 66
<212> TYPE: PRT
<213> ORGANISM: Artificial Sequence
<220> FEATURE:
<223> OTHER INFORMATION: Ascaris trypsin inhibitor

<400> SEQUENCE: 22

Glu Ala Glu Lys Cys Asx Glx Glx Pro Gly Trp Thr Lys Gly Gly Cys
1               5                   10                  15

Glu Thr Cys Gly Cys Ala Gln Lys Ile Val Pro Cys Thr Arg Glu Thr
            20                  25                  30

Lys Pro Asn Pro Gln Cys Pro Arg Lys Gln Cys Cys Ile Ala Ser Ala
        35                  40                  45

Gly Phe Val Arg Asp Ala Gln Gly Asn Cys Ile Lys Phe Glu Asp Cys
    50                  55                  60

Pro Lys
65

<210> SEQ ID NO 23
<211> LENGTH: 62
<212> TYPE: PRT
<213> ORGANISM: Artificial Sequence
<220> FEATURE:
<223> OTHER INFORMATION: Ascaris trypsin inhibitor

<400> SEQUENCE: 23

Glu Ala Glu Lys Cys Thr Lys Pro Asn Glu Gln Trp Thr Lys Cys Gly
1               5                   10                  15

Gly Cys Glu Gly Thr Cys Ala Gln Lys Ile Val Pro Cys Thr Arg Glu
            20                  25                  30

Cys Lys Pro Pro Arg Cys Glu Cys Ile Ala Ser Ala Gly Phe Val Arg
        35                  40                  45

Asp Ala Gln Gly Asn Cys Ile Lys Phe Glu Asp Cys Pro Lys
    50                  55                  60
```

<210> SEQ ID NO 24
<211> LENGTH: 101
<212> TYPE: PRT
<213> ORGANISM: Artificial Sequence
<220> FEATURE:
<223> OTHER INFORMATION: Onion trypsin inhibitor

<400> SEQUENCE: 24

```
Met Lys Ala Ala Leu Val Ile Phe Leu Leu Ile Ala Met Leu Gly Val
1               5                   10                  15

Leu Ala Ala Glu Ala Tyr Pro Asn Leu Arg Gln Val Val Thr Gly
            20                  25                  30

Asp Glu Glu Gly Gly Cys Cys Asp Ser Cys Gly Ser Cys Asp Arg
        35                  40                  45

Arg Ala Pro Asp Leu Ala Arg Cys Glu Cys Arg Asp Val Val Thr Ser
    50                  55                  60

Cys Gly Pro Gly Cys Lys Arg Cys Glu Ala Asp Leu Asp Leu Asn
65              70                  75                  80

Pro Pro Arg Tyr Val Cys Lys Asp Met Ser Phe His Ser Cys Gln Thr
                85                  90                  95

Arg Cys Ser Ile Leu
            100
```

<210> SEQ ID NO 25
<211> LENGTH: 84
<212> TYPE: PRT
<213> ORGANISM: Artificial Sequence
<220> FEATURE:
<223> OTHER INFORMATION: Barley chymotrypsin inhibitor 2

<400> SEQUENCE: 25

```
Met Ser Ser Met Glu Lys Lys Pro Glu Gly Val Asn Ile Gly Ala Gly
1               5                   10                  15

Asp Arg Gln Asn Gln Lys Thr Glu Trp Pro Glu Leu Val Gly Lys Ser
            20                  25                  30

Val Glu Glu Ala Lys Lys Val Ile Leu Gln Asp Lys Pro Ala Ala Gln
        35                  40                  45

Ile Ile Val Leu Pro Val Gly Thr Ile Val Thr Met Glu Tyr Arg Ile
    50                  55                  60

Asp Arg Val Arg Leu Phe Val Asp Arg Leu Asp Asn Ile Ala Gln Val
65              70                  75                  80

Pro Arg Val Gly
```

<210> SEQ ID NO 26
<211> LENGTH: 26
<212> TYPE: PRT
<213> ORGANISM: Staphylococcus aureus

<400> SEQUENCE: 26

```
Met Ala Gln Asp Ile Ile Ser Thr Ile Ser Asp Leu Val Lys Trp Ile
1               5                   10                  15

Ile Asp Thr Val Asn Lys Phe Thr Lys Lys
            20                  25
```

<210> SEQ ID NO 27
<211> LENGTH: 26
<212> TYPE: PRT
<213> ORGANISM: Staphylococcus epidermidis

<400> SEQUENCE: 27

Met Met Ala Ala Asp Ile Ile Ser Thr Ile Gly Asp Leu Val Lys Trp
1               5                   10                  15

Ile Ile Asp Thr Val Asn Lys Phe Lys Lys
            20                  25

<210> SEQ ID NO 28
<211> LENGTH: 26
<212> TYPE: PRT
<213> ORGANISM: Staphylococcus aureus

<400> SEQUENCE: 28

Met Ala Gln Asp Ile Ile Ser Thr Ile Ser Asp Leu Val Lys Trp Ile
1               5                   10                  15

Ile Asp Thr Val Asn Lys Phe Thr Lys Lys
            20                  25

<210> SEQ ID NO 29
<211> LENGTH: 21
<212> TYPE: PRT
<213> ORGANISM: Artificial Sequence
<220> FEATURE:
<223> OTHER INFORMATION: PSM-alpha-1

<400> SEQUENCE: 29

Met Gly Ile Ile Ala Gly Ile Ile Lys Val Ile Lys Ser Leu Ile Glu
1               5                   10                  15

Gln Phe Thr Gly Lys
            20

<210> SEQ ID NO 30
<211> LENGTH: 21
<212> TYPE: PRT
<213> ORGANISM: Artificial Sequence
<220> FEATURE:
<223> OTHER INFORMATION: PSM-alpha-2

<400> SEQUENCE: 30

Met Gly Ile Ile Ala Gly Ile Ile Lys Phe Ile Lys Gly Leu Ile Glu
1               5                   10                  15

Lys Phe Thr Gly Lys
            20

<210> SEQ ID NO 31
<211> LENGTH: 22
<212> TYPE: PRT
<213> ORGANISM: Artificial Sequence
<220> FEATURE:
<223> OTHER INFORMATION: PSM-alpha-3

<400> SEQUENCE: 31

Met Glu Phe Val Ala Lys Leu Phe Lys Phe Phe Lys Asp Leu Leu Gly
1               5                   10                  15

Lys Phe Leu Gly Asn Asn
            20

<210> SEQ ID NO 32
<211> LENGTH: 20
<212> TYPE: PRT
<213> ORGANISM: Artificial Sequence
<220> FEATURE:
<223> OTHER INFORMATION: PSM-alpha-4

<400> SEQUENCE: 32

```
Met Ala Ile Val Gly Thr Ile Ile Lys Ile Ile Lys Ala Ile Ile Asp
1               5                   10                  15

Ile Phe Ala Lys
            20
```

<210> SEQ ID NO 33
<211> LENGTH: 44
<212> TYPE: PRT
<213> ORGANISM: Artificial Sequence
<220> FEATURE:
<223> OTHER INFORMATION: PSM-beta-1

<400> SEQUENCE: 33

```
Met Glu Gly Leu Phe Asn Ala Ile Lys Asp Thr Val Thr Ala Ala Ile
1               5                   10                  15

Asn Asn Asp Gly Ala Lys Leu Gly Thr Ser Ile Val Ser Ile Val Glu
            20                  25                  30

Asn Gly Val Gly Leu Leu Gly Lys Leu Phe Gly Phe
            35                  40
```

<210> SEQ ID NO 34
<211> LENGTH: 44
<212> TYPE: PRT
<213> ORGANISM: Artificial Sequence
<220> FEATURE:
<223> OTHER INFORMATION: PSM-beta-2

<400> SEQUENCE: 34

```
Met Thr Gly Leu Ala Glu Ala Ile Ala Asn Thr Val Gln Ala Ala Gln
1               5                   10                  15

Gln His Asp Ser Val Lys Leu Gly Thr Ser Ile Val Asp Ile Val Ala
            20                  25                  30

Asn Gly Val Gly Leu Leu Gly Lys Leu Phe Gly Phe
            35                  40
```

<210> SEQ ID NO 35
<211> LENGTH: 232
<212> TYPE: PRT
<213> ORGANISM: Escherichia coli

<400> SEQUENCE: 35

```
Met Ser Gly Gly Asp Gly Arg Gly His Asn Thr Gly Ala His Ser Thr
1               5                   10                  15

Ser Gly Asn Ile Asn Gly Gly Pro Thr Gly Leu Gly Val Gly Gly Gly
            20                  25                  30

Ala Ser Asp Gly Ser Gly Trp Ser Ser Glu Asn Asn Pro Trp Gly Gly
            35                  40                  45

Gly Ser Gly Ser Gly Ile His Trp Gly Gly Ser Gly His Gly Asn
        50                  55                  60

Gly Gly Gly Asn Gly Asn Ser Gly Gly Ser Gly Thr Gly Gly Asn
65                  70                  75                  80

Leu Ser Ala Val Ala Ala Pro Val Ala Phe Gly Phe Pro Ala Leu Ser
                85                  90                  95

Thr Pro Gly Ala Gly Gly Leu Ala Val Ser Ile Ser Ala Gly Ala Leu
            100                 105                 110

Ser Ala Ala Ile Ala Asp Ile Met Ala Ala Leu Lys Gly Pro Phe Lys
            115                 120                 125

Phe Gly Leu Trp Gly Val Ala Leu Tyr Gly Val Leu Pro Ser Gln Ile
            130                 135                 140
```

```
Ala Lys Asp Asp Pro Asn Met Met Ser Lys Ile Val Thr Ser Leu Pro
145                 150                 155                 160

Ala Asp Asp Ile Thr Glu Ser Pro Val Ser Ser Leu Pro Leu Asp Lys
                165                 170                 175

Ala Thr Val Asn Val Asn Val Arg Val Val Asp Asp Val Lys Asp Glu
            180                 185                 190

Arg Gln Asn Ile Ser Val Val Ser Gly Val Pro Met Ser Val Pro Val
        195                 200                 205

Val Asp Ala Lys Pro Thr Glu Arg Pro Gly Val Phe Thr Ala Ser Ile
    210                 215                 220

Pro Gly Ala Pro Val Leu Asn Ile
225                 230

<210> SEQ ID NO 36
<211> LENGTH: 511
<212> TYPE: PRT
<213> ORGANISM: Artificial Sequence
<220> FEATURE:
<223> OTHER INFORMATION: HA1 fragment containing an initiating
      methionine and artificial second codon but without the initial
      signal sequence, an altered protease cleavage site and membrane
      anchor truncation

<400> SEQUENCE: 36

Met Ala Thr Phe Ala Thr Ala Asn Ala Asp Thr Leu Cys Ile Gly Tyr
1               5                   10                  15

His Ala Asn Asn Ser Thr Asp Thr Val Asp Thr Val Leu Glu Lys Asn
            20                  25                  30

Val Thr Val Thr His Ser Val Asn Leu Leu Glu Asp Lys His Asn Gly
        35                  40                  45

Lys Leu Cys Lys Leu Arg Gly Val Ala Pro Leu His Leu Gly Lys Cys
    50                  55                  60

Asn Ile Ala Gly Trp Ile Leu Gly Asn Pro Glu Cys Glu Ser Leu Ser
65                  70                  75                  80

Thr Ala Ser Ser Trp Ser Tyr Ile Val Glu Thr Ser Ser Ser Asp Asn
                85                  90                  95

Gly Thr Cys Tyr Pro Gly Asp Phe Ile Asp Tyr Glu Glu Leu Arg Glu
            100                 105                 110

Gln Leu Ser Ser Val Ser Ser Phe Glu Arg Phe Glu Ile Phe Pro Lys
        115                 120                 125

Thr Ser Ser Trp Pro Asn His Asp Ser Asn Lys Gly Val Thr Ala Ala
    130                 135                 140

Cys Pro His Ala Gly Ala Lys Ser Phe Tyr Lys Asn Leu Ile Trp Leu
145                 150                 155                 160

Val Lys Lys Gly Asn Ser Tyr Pro Lys Leu Ser Lys Ser Tyr Ile Asn
                165                 170                 175

Asp Lys Gly Lys Glu Val Leu Val Leu Trp Gly Ile His His Pro Ser
            180                 185                 190

Thr Ser Ala Asp Gln Gln Ser Leu Tyr Gln Asn Ala Asp Ala Tyr Val
        195                 200                 205

Phe Val Gly Ser Ser Arg Tyr Ser Lys Lys Phe Lys Pro Glu Ile Ala
    210                 215                 220

Ile Arg Pro Lys Val Arg Asp Gln Glu Gly Arg Met Asn Tyr Tyr Trp
225                 230                 235                 240

Thr Leu Val Glu Pro Gly Asp Lys Ile Thr Phe Glu Ala Thr Gly Asn
                245                 250                 255
```

Leu Val Val Pro Arg Tyr Ala Phe Ala Met Glu Arg Asn Ala Gly Ser
                260                 265                 270

Gly Ile Ile Ile Ser Asp Thr Pro Val His Asp Cys Asn Thr Thr Cys
            275                 280                 285

Gln Thr Pro Lys Gly Ala Ile Asn Thr Ser Leu Pro Phe Gln Asn Ile
    290                 295                 300

His Pro Ile Thr Ile Gly Lys Cys Pro Lys Tyr Val Lys Ser Thr Lys
305                 310                 315                 320

Leu Arg Leu Ala Thr Gly Leu Arg Asn Val Pro Ser Ile Gln Ser Thr
                325                 330                 335

Gly Leu Phe Gly Ala Ile Ala Gly Phe Ile Glu Gly Gly Trp Thr Gly
            340                 345                 350

Met Val Asp Gly Trp Tyr Gly Tyr His His Gln Asn Glu Gln Gly Ser
        355                 360                 365

Gly Tyr Ala Ala Asp Leu Lys Ser Thr Gln Asn Ala Ile Asp Glu Ile
    370                 375                 380

Thr Asn Lys Val Asn Ser Val Ile Glu Lys Met Asn Thr Gln Phe Thr
385                 390                 395                 400

Ala Val Gly Lys Glu Phe Asn His Leu Glu Lys Arg Ile Glu Asn Leu
                405                 410                 415

Asn Lys Lys Val Asp Asp Gly Phe Leu Asp Ile Trp Thr Tyr Asn Ala
            420                 425                 430

Glu Leu Leu Val Leu Leu Glu Asn Glu Arg Thr Leu Asp Tyr His Asp
        435                 440                 445

Ser Asn Val Lys Asn Leu Tyr Glu Lys Val Arg Ser Gln Leu Lys Asn
450                 455                 460

Asn Ala Lys Glu Ile Gly Asn Gly Cys Phe Glu Phe Tyr His Lys Cys
465                 470                 475                 480

Asp Asn Thr Cys Met Glu Ser Val Lys Asn Gly Thr Tyr Asp Tyr Pro
                485                 490                 495

Lys Tyr Ser Glu Glu Ala Lys Leu Asn Arg Glu Glu Ile Asp Gly
            500                 505                 510

<210> SEQ ID NO 37
<211> LENGTH: 47
<212> TYPE: PRT
<213> ORGANISM: Escherichia coli

<400> SEQUENCE: 37

Met Lys Lys Ile Thr Gly Ile Ile Leu Leu Leu Leu Ala Val Ile Ile
1               5                   10                  15

Leu Ser Ala Cys Gln Ala Asn Tyr Ile Arg Asp Val Gln Gly Gly Thr
            20                  25                  30

Val Ser Pro Ser Ser Thr Ala Glu Val Thr Gly Leu Ala Thr Gln
        35                  40                  45

<210> SEQ ID NO 38
<211> LENGTH: 61
<212> TYPE: PRT
<213> ORGANISM: Artificial Sequence
<220> FEATURE:
<223> OTHER INFORMATION: Ascaris chymotrypsin and elastase inhibitor

<400> SEQUENCE: 38

Gly Gln Glu Ser Cys Gly Pro Asn Glu Val Trp Thr Glu Cys Thr Gly
1               5                   10                  15

Cys Glu Met Lys Cys Gly Pro Asp Glu Asn Thr Pro Cys Pro Leu Met

```
            20                  25                  30

Cys Arg Arg Pro Ser Cys Glu Cys Ser Pro Gly Arg Gly Met Arg Arg
            35                  40                  45

Thr Asn Asp Gly Lys Cys Ile Pro Ala Ser Gln Cys Pro
            50                  55                  60

<210> SEQ ID NO 39
<211> LENGTH: 60
<212> TYPE: PRT
<213> ORGANISM: Artificial Sequence
<220> FEATURE:
<223> OTHER INFORMATION: C-terminal signal sequence of hlyA

<400> SEQUENCE: 39

Ser Thr Tyr Gly Ser Gln Asp Tyr Leu Asn Pro Leu Ile Asn Glu Ile
1               5                   10                  15

Ser Lys Ile Ile Ser Ala Ala Gly Asn Leu Asp Val Lys Glu Glu Arg
            20                  25                  30

Ser Ala Ala Ser Leu Leu Gln Leu Ser Gly Asn Ala Ser Asp Phe Ser
            35                  40                  45

Tyr Gly Arg Asn Ser Ile Thr Leu Thr Ala Ser Ala
            50                  55                  60

<210> SEQ ID NO 40
<211> LENGTH: 61
<212> TYPE: PRT
<213> ORGANISM: Artificial Sequence
<220> FEATURE:
<223> OTHER INFORMATION: Ascaris chymotrypsin and elastase inhibitor

<400> SEQUENCE: 40

Gly Gln Glu Ser Cys Gly Pro Asn Glu Val Trp Thr Glu Cys Thr Gly
1               5                   10                  15

Cys Glu Met Lys Cys Gly Pro Asp Glu Asn Thr Pro Cys Pro Leu Met
            20                  25                  30

Cys Arg Arg Pro Ser Cys Glu Cys Ser Pro Gly Arg Gly Met Arg Arg
            35                  40                  45

Thr Asn Asp Gly Lys Cys Ile Pro Ala Ser Gln Cys Pro
            50                  55                  60

<210> SEQ ID NO 41
<211> LENGTH: 60
<212> TYPE: PRT
<213> ORGANISM: Artificial Sequence
<220> FEATURE:
<223> OTHER INFORMATION: C-terminal signal sequence of hlyA

<400> SEQUENCE: 41

Ser Thr Tyr Gly Ser Gln Asp Tyr Leu Asn Pro Leu Ile Asn Glu Ile
1               5                   10                  15

Ser Lys Ile Ile Ser Ala Ala Gly Asn Leu Asp Val Lys Glu Glu Arg
            20                  25                  30

Ser Ala Ala Ser Leu Leu Gln Leu Ser Gly Asn Ala Ser Asp Phe Ser
            35                  40                  45

Tyr Gly Arg Asn Ser Ile Thr Leu Thr Ala Ser Ala
            50                  55                  60

<210> SEQ ID NO 42
<211> LENGTH: 18
<212> TYPE: PRT
<213> ORGANISM: Artificial Sequence
```

<220> FEATURE:
<223> OTHER INFORMATION: N-terminal signal sequence from M13pIII

<400> SEQUENCE: 42

Met Lys Lys Leu Leu Phe Ala Ile Pro Leu Val Val Pro Phe Tyr Ser
1               5                   10                  15

His Ser

<210> SEQ ID NO 43
<211> LENGTH: 61
<212> TYPE: PRT
<213> ORGANISM: Artificial Sequence
<220> FEATURE:
<223> OTHER INFORMATION: Ascaris chymotrypsin and elastase inhibitor

<400> SEQUENCE: 43

Gly Gln Glu Ser Cys Gly Pro Asn Glu Val Trp Thr Glu Cys Thr Gly
1               5                   10                  15

Cys Glu Met Lys Cys Gly Pro Asp Glu Asn Thr Pro Cys Pro Leu Met
            20                  25                  30

Cys Arg Arg Pro Ser Cys Glu Cys Ser Pro Gly Arg Gly Met Arg Arg
        35                  40                  45

Thr Asn Asp Gly Lys Cys Ile Pro Ala Ser Gln Cys Pro
    50                  55                  60

<210> SEQ ID NO 44
<211> LENGTH: 47
<212> TYPE: PRT
<213> ORGANISM: Artificial Sequence
<220> FEATURE:
<223> OTHER INFORMATION: colE3 colicin release protein

<400> SEQUENCE: 44

Met Lys Lys Ile Thr Gly Ile Ile Leu Leu Leu Leu Ala Val Ile Ile
1               5                   10                  15

Leu Ser Ala Cys Gln Ala Asn Tyr Ile Arg Asp Val Gln Gly Gly Thr
            20                  25                  30

Val Ser Pro Ser Ser Thr Ala Glu Val Thr Gly Leu Ala Thr Gln
        35                  40                  45

<210> SEQ ID NO 45
<211> LENGTH: 7
<212> TYPE: PRT
<213> ORGANISM: Artificial Sequence
<220> FEATURE:
<223> OTHER INFORMATION: In-frame fusion for a bacterium directed toward
      malaria

<400> SEQUENCE: 45

Glu Thr Thr Leu Lys Ser Phe
1               5

<210> SEQ ID NO 46
<211> LENGTH: 60
<212> TYPE: PRT
<213> ORGANISM: Artificial Sequence
<220> FEATURE:
<223> OTHER INFORMATION: C-terminal signal sequence of hlyA

<400> SEQUENCE: 46

Ser Thr Tyr Gly Ser Gln Asp Tyr Leu Asn Pro Leu Ile Asn Glu Ile
1               5                   10                  15

Ser Lys Ile Ile Ser Ala Ala Gly Asn Leu Asp Val Lys Glu Glu Arg

```
                  20                  25                  30
Ser Ala Ala Ser Leu Leu Gln Leu Ser Gly Asn Ala Ser Asp Phe Ser
         35                  40                  45

Tyr Gly Arg Asn Ser Ile Thr Leu Thr Ala Ser Ala
     50                  55                  60

<210> SEQ ID NO 47
<211> LENGTH: 8
<212> TYPE: PRT
<213> ORGANISM: Artificial Sequence
<220> FEATURE:
<223> OTHER INFORMATION: Trypsin cleaveage signal

<400> SEQUENCE: 47

Phe Gln Asn Ala Leu Leu Val Arg
1               5

<210> SEQ ID NO 48
<211> LENGTH: 14
<212> TYPE: PRT
<213> ORGANISM: Artificial Sequence
<220> FEATURE:
<223> OTHER INFORMATION: Protease Inhibitor 15, corresponding to amino
      acids 245-258 of human protease inhibitor

<400> SEQUENCE: 48

Cys Phe Pro Gly Val Thr Ser Asn Tyr Leu Tyr Trp Phe Lys
1               5                   10

<210> SEQ ID NO 49
<211> LENGTH: 4
<212> TYPE: PRT
<213> ORGANISM: Artificial Sequence
<220> FEATURE:
<223> OTHER INFORMATION: Factor Xa cleavage site

<400> SEQUENCE: 49

Ile Glu Gly Arg
1

<210> SEQ ID NO 50
<211> LENGTH: 5
<212> TYPE: PRT
<213> ORGANISM: Artificial Sequence
<220> FEATURE:
<223> OTHER INFORMATION: Chymotrypsin cleavage site (low specificity)

<400> SEQUENCE: 50

Phe Tyr Trp Met Leu
1               5

<210> SEQ ID NO 51
<211> LENGTH: 4
<212> TYPE: PRT
<213> ORGANISM: Artificial Sequence
<220> FEATURE:
<223> OTHER INFORMATION: Protozoan

<400> SEQUENCE: 51

Arg Gly Asp Ser
1
```